United States Patent [19]
Austin et al.

[11] Patent Number: 6,132,965
[45] Date of Patent: *Oct. 17, 2000

[54] METHODS AND COMPOSITIONS FOR DIAGNOSIS OF HYPERHOMOCYSTEINEMIA

[75] Inventors: Richard C. Austin, Ancaster; Jack Hirsh; Jeffrey I. Weitz, both of Hamilton, all of Canada

[73] Assignee: Hamilton Civic Hospitals Research Development Inc., Canada

[*] Notice: This patent is subject to a terminal disclaimer.

[21] Appl. No.: 09/016,540

[22] Filed: Jan. 30, 1998

Related U.S. Application Data

[63] Continuation of application No. 08/582,261, Jan. 3, 1996.
[51] Int. Cl.$^7$ .............. C07H 21/04; C12Q 1/68
[52] U.S. Cl. ............. 435/6; 435/91.2; 536/23.1; 536/24.3; 536/24.33
[58] Field of Search ............ 435/6, 91.2; 536/23.1, 536/24.3, 24.33

[56] References Cited

U.S. PATENT DOCUMENTS 5,817,461 10/1998 Austin et al. .............. 435/6

FOREIGN PATENT DOCUMENTS

97/25440 7/1997 WIPO .............. C12Q 1/68

*Primary Examiner*—George C. Elliott
*Assistant Examiner*—Janet Epps
*Attorney, Agent, or Firm*—Townsend & Townsend & Crew LLP

[57] ABSTRACT

A method for diagnosing hyperhomocysteinemia by molecular genetic means is disclosed.

3 Claims, 5 Drawing Sheets

FIG. 5A.

```
T7MGAP1B.SEQ       AAATCAGAATAGGTGTTGGTATAGAATGGGGTCTCCTCCGGCGGGGTCGAAGAAGT
                           10        20        30        40        50        60
                   X:::::::::::::::::::::::::::::::::::::::::::::::::::::::::
M62278             AAATCAGAATAGGTGTTGGTATAGAATGGGGTCTCCTCCGGCGGGGTCGAAGAAGT
                           20        30        40        50        60        70

T7MGAP1B.SEQ       GGTGTTGAGGTTGCGGTGAGGTTTTGATCACTCTGGGTGACAGAGTGAGACCCTGTCCC
                           70        80        90       100       110
                   :::::::::::::::::::X : :
M62278             GGTGTTGAGGTTGCGGTGCTGTTAGTAGTATAGTGATGCCAGCAGCTAGGACTGGGACAG
                           80        90       100       110       120       130
```

FIG. 5B.

FILE NAME: T7MGAP1B.SEQ    SEQUENCE:119BP; 24A; 21C; 43G; 31T; RANGE:1-119
MODE:NORMAL    CUTOFF:100    KTUP:4    TARGET:GenBank#1 databaseRELEASE:R86.0
GROUP NAME:   Primate, Rodent, Other Mammalian, Other Vertebrate, Expressed
Found: 13, Optimized: 13

| NO. | TARGET FILE | DEFINITION | MATCH% | OVER. | INIT | OPT |
|---|---|---|---|---|---|---|
| 1 | M62278 | EST00349 HOMO SAPIENS cDNA CLONE HHCJ6 | 96.3 | 82 | 308 | 310 |
| 2 | MUSCKM1 | MOUSE MUSCLE-SPECIFIC FORM OF CREATINE | 61.4 | 70 | 114 | 118 |
| 3 | MUSMCKA | MOUSE MUSCLE CREATINE KINASE (MCK) GEN | 61.4 | 70 | 114 | 118 |
| 4 | T07031 | EST04920 HOMO SAPIENS cDNA CLONE HFBEC | 57.9 | 76 | 110 | 116 |
| 5 | HUMVMLC | HUMAN VENTRICULAR MYOZIN LIGHT CHAIN 2 | 67.9 | 56 | 108 | 116 |
| 6 | HSYMYCLC2 | H.SAPIENS GENE FOR VENTRICULAR MYOSIN | 67.9 | 56 | 108 | 116 |
| 7 | UMGABRB1S4 | HUMAN GAMMA-AMINOBUTYRIC ACID-A (GABA- | 53.5 | 101 | 104 | 112 |
| 8 | HSMFD36 | HUMAN MFD36 DINUCLEOTIDE REPEAT DNA. | 100.0 | 26 | 104 | 104 |
| 9 | HUMRETBLAS | HUMAN RETINOBLASTOMA SUSCEPTIBILITY GE | 58.8 | 102 | 104 | 134 |
| 10 | HSMFD36 | H.SAPIENS SEQUENCE INVOLVED IN X;Y TRA | 54.1 | 98 | 104 | 122 |
| 11 | CHKHSPA | CHICKEN 108K HEAT SHOCK PROTEIN GENE, | 59.6 | 89 | 102 | 120 |
| 12 | GGHSP108 | HEN GENE FOR STEROID INDUCIBLE 108K HE | 59.6 | 89 | 102 | 120 |
| 13 | HUM9DC89Z | HOMO SAPIENS (SUBCLONE H9_8_g2 FROM P1 | 58.0 | 119 | 102 | 146 |

METHODS AND COMPOSITIONS FOR DIAGNOSIS OF HYPERHOMOCYSTEINEMIA

This application is a continuation of U.S. application Ser. No. 08/582,261, filed Jan. 3, 1996, the disclosure of which is incorporated herein by reference in its entirety.

FIELD OF THE INVENTION

The invention relates to methods for identifying genes which are transcriptionally modulated by the level of extracellular homocysteine or other metabolites characteristic of hyperhomocystenemia, and/or which correlate with the pathological condition of homocysteinemia. The invention relates to polynucleotides, polypeptides, diagnostic methods and compositions, gene therapy methods and compositions, and antibodies, and other related embodiments. The present invention provides a novel method for enriching, isolating, and identifying polynucleotide sequences of low abundance RNA species which are differentially expressed in individuals having elevated levels of serum homocysteine. The invention provides methods and compositions relating to the fields of molecular biology, chemistry, pharmacology, and medical and diagnostic technology.

BACKGROUND AND DESCRIPTION OF RELATED ART

Homocysteinemia and Related Pathology

Cardiovascular disease due to atherosclerosis, and arterial and venous thromboembolism are a major cause of mortality and morbidity in North America. Although conventional risk factors such as hypercholesterolemia, hypertension and smoking are associated with increased risk for cardiovascular disease, they do not account for all cases. There is mounting evidence that elevated blood levels of homocysteine (hyperhomocysteinemia) represent a significant risk factor for premature vascular and thrombotic disease. Hyperhomocysteinemia has been found in approximately 20–30% of individuals identified with coronary artery disease, peripheral vascular disease and stroke (Boers et al. (1985) *N. Engl. J. Med.* 313: 709; Clarke et al. (1991) *N. Engl. J. Med.* 324: 1149; Sethub et al. (1995) *N. Engl. J. Med.* 332: 286; den Heijer et al. (1995) *Lancet* 345: 882. Despite the fact that a number of inherited or acquired conditions can lead to hyperhomocysteinemia, the relationship between increased homocysteine levels and vascular disease is present regardless of the underlying metabolic causes.

The majority of inherited cases are believed to result from deficiency of the enzyme cystathionine β-synthase, which mediates the condensation of homocysteine with serine to form cystathionine. Individuals homozygous for cystathionine β-synthase deficiency suffer from ocular, skeletal and neurologic complications, and are at high risk for premature vascular disease and venous thrombosis (Mudd et al. (1981) *Am. J. Hum. Genet.* 33: 883; Ueland et al. (1989) *J. Lab. Clin. Med.* 114: 473; Ueland et al. *Plasma homocysteine and cardiovascular disease.* in *Atherosclerotic Cardiovascuar Disease, Hemostasis, and Endothelial Function* Francis R B, Ed. (1993) Marcel Dekker, Inc., pp. 183–236). The homozygous form of cystathionine β-synthase deficiency is associated with a 9% incidence of myocardial infarction, a 38% incidence of thromboembolic disease and a 23% incidence of cerebrovascular and frequent peripheral vascular events (Grieco et al. (1977) *Am. J. Med. Sci.* 273: 120). Despite the autosomal recessive inheritance, there now is evidence for an association between heterozygosity for cystathionine β-synthase deficiency and premature vascular disease (Clarke et al. (1991) op.cit; Boers et al. (1985) op.cit; Malinow et al. (1989) *Circulation* 79: 1180; Kang et al. (1986) *J. Clin. Invest.* 77: 1482). Based on the frequency of the homozygous condition at birth, it is estimated that at least 1–2 percent of the population (not including individuals with other different types of acquired or inherited abnormalities of homocysteine catabolism) has hyperhomocysteinemia and are at risk for premature vascular disease and thrombosis.

Although the identification of homozygous cystathionine β-synthase deficiency can be made on the basis of markedly elevated plasma levels of homocysteine, this means of diagnosis is inconvenient and is poorly suited for identifying the more common heterozygous state because plasma homocysteine levels in heterozygous individuals can overlap with those found in healthy individuals (McGill et al. (1990) *Am. J. Med. Genet.* 36: 45). This problem can be partially circumvented using a methionine-loading test in which L-methionine is given orally after an overnight fast. Venous blood samples are obtained immediately before and four to eight hours after methionine administration for measurement of serum non-protein bound homocysteine. Homocysteine levels are then determined using ion-exchange chromatography. This approach is both time-consuming and uncomfortable for the patient and fails to identify all heterozygotes (Boers et al. (1985) op.cit; Kang et al. (1986) op.cit). Other methods are available to identify heterozygotes but these are even more problematic. For example, the activity of cystathionine β-synthase can be determined from cultured fibroblasts but this requires a skin biopsy, an invasive procedure. Recently, a bacterial screening-expression system has been developed to identify patients with hyperhomocysteinemia caused exclusively by cystathionine β-synthase deficiency (Kozich and Kraus (1992) *Hum. Mut.* 1: 113). This system also allows for the characterization of the mutation within the cystathionine β-synthase gene. There are, however, at least two major disadvantages with this approach. Firstly, it can only be used to identify individuals deficient in the enzyme cystathionine β-synthase. Therefore, patients with other forms of genetic or acquired conditions which predispose them to hyperhomocysteinemia cannot be identified. Secondly, allelic and genetic heterogeneity within the cystathionine β-synthase gene complicates the reliable use of this approach.

At present, there is no simple and reliable test to identify individuals with hyperhomocysteinemia. This is a serious drawback because some forms of hyperhomocysteinemia can often be corrected by vitamin supplementation (Ubbink et al. (1993) *Clin. Invest.* 71: 993; Franken et al. (1994) *Arteroscler. Thromb.* 14: 465. Since such treatment results in only minor side effects, it is important to identify the individuals at risk for hyperhomocysteinemia so that they can be targeted for treatment aimed at reducing plasma homocysteine, thereby reducing the risk of vascular disease. Furthermore a simple diagnostic test would provide a method to monitor the success of such treatment and its impact on subsequent atherosclerosis.

Despite intensive study the exact mechanisms responsible for homocysteine-induced vascular disease remain unclear. However, several recent reports have shown that homocysteine contributes to endothelial cell damage and dysfunction in vitro. These include induction of a protease activator of Factor V (Rodgers and Kane (1986) *J. Clin. Invest.* 77: 1909), induction of an inhibitor of protein C activation (Rodgers and Conn (1990) *Blood* 75: 895), aberrant processing and secretion of thrombomodulin (Lentz and Sadler (1991) *J. Clin. Invest.* 88: 1906) and von Willebrand Factor (Lentz and Sadler (1993) *Blood* 81: 683), and inhibition of thrombomodulin cofactor activity (Hayashi et al. (1992) *Blood* 79; 2930). Alteratively, homocysteine may promote the proliferation of vascular smooth muscle cells, a major component in atherosclerotic plaque, while decreasing endothelial cell proliferation (Tsai et al. (1994) *Proc. Natl. Acad. Sci. (U.S.A.)* 91; 6369). Marked platelet accumulation at sites of vascular injury and platelet rich occlusive thrombi are also distinctive pathologic features of both human and experimental hyperhomocysteinemia (James et al. (1990) *J. Am. Coll. Cardiol.* 15: 763; Harker et al. (1983) *Circ. Res.* 53: 731). In addition, platelet survival appears to be shortened in patients with hyperhomocysteinemia. However, the mechanisms involved in homocysteine-induced platelet dysfunction also remain elusive.

The diagnosis of cardiovascular disease requires a detailed clinical evaluation, and diagnosis generally cannot be made until significant symptoms of coronary artery occlusion and plaque formation are clinically apparent. Thus, there is a need for a simple and reliable diagnostic method for hyperhomocysteinemia, which is associated with a substantial fraction of atherosclerotic disease patients, and for methods to use such tests to identify patients with hyperhomocysteinemia and monitor the effect of pharmacologic interventions on homocysteine-induced pathology.

Enrichment Cloning Methods and Differential RNA Display

Selective amplification of polynucleotides represents a major research goal of molecular biology, with particular importance in diagnostic and forensic applications, as well as for general manipulations of genetic materials and laboratory reagents.

Comparisons of gene expression in different cell types or in a single cell type under different conditions provides a basis for analyzing the underlying biological processes controlling cell differentiation and metabolism, and can be used as a pathognomonic indicator of a pathological condition or predisposition to developing a pathological condition.

One way to compare gene expression between two cell populations in vitro or in vivo is to identify mRNA species which are differentially expressed between the cell populations (i.e., present at different abundances between the cell populations). Current methods that distinguish mRNAs in comparative studies largely rely on subtractive hybridization (Lee et al. (1991) *Proc. Natl. Acad. Sci. (U.S.A.)* 88: 2825) or differential display employing arbitrary primer polymerase chain reaction (PCR) (Liang and Pardee (1992) *Science* 257: 967). Each of these methods has been used by various investigators to identify differentially expressed mRNA species, including mRNAs which have increased or decreased abundance in cancer cells (Salesiotis et al. (1995) *Cancer Lett.* 91: 47; Jiang et al. (1995) *Oncogene* 10: 1855; Blok et al. (1995) *Prostate* 26: 213; Shinoura et al. (1995) *Cancer Lett.* 89: 215; Murphy et al. (1993) *Cell Growth Differ.* 4: 715; Austruy et al. (1993) *Cancer Res.* 53: 2888; Zhang et al. (1993) *Mol. Carcinog.* 8: 123; and Liang et al. (1992) *Cancer Res.* 52: 6966). The methods have also been used to identify mRNA species which are induced or repressed by drugs or certain nutrients (Fisicaro et al. (1995) *Mol. Immunol.* 32: 565; Chapman et al. (1995) *Mol. Cell. Endocrinol.* 108: 108; Douglass et al. (1995) *J. Neurosci.* 15: 2471; Aiello et al. (1994) *Proc. Natl. Acad. Sci. (U.S.A.)* 91: 6231; Ace et al. (1994) *Endocrinology* 134: 1305. However, there are no reports of these methods being used to identify mRNA species which are differentially expressed in cells exposed to hyperphysiological levels of homocysteine either in vitro or in vivo.

Since no in vitro biochemical diagnostic test is presently available for rapidly and conveniently diagnosing hyperhomocysteinemia in its early stages and for identifying disease candidates, there is a need for the identification of polynucleotides (e.g., cDNA species) which are aberrently expressed in a cell sample (e.g., white blood cells or platelets isolated from peripheral blood) from a patient having hyperhomocysteinemia. These polynucleotides and the encoded polypeptides can be used in methods to identify patients with hyperhomocysteinemia, to monitor the effect of pharmacologic interventions on homocysteine-induced pathology, for gene therapy vectors and as ptoential targets for drug development assays, among other uses.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference, whether specifically noted as such or not.

SUMMARY OF THE INVENTION

The present invention provides compositions and methods for the diagnosis and treatment of atherosclerotic diseases and diseases of metabolism of sulfur-containing amino acids (e.g., homocysteinemia) which are associated with vascular damage and atherosclerotic disease.

The invention provides genetic and immunological markers for the successful diagnosis and treatment of homocysteine-induced vascular disease, and methods employing these markers to monitor the success of interventions which are intended to lower plasma homocysteine levels. The genetic and immunological markers are also used to identify therapies which will be beneficial with respect to recurrent vascular disease and thrombosis related to hyperhomocystenemia and provide a basis for developing pharmaceutical agents which, when administered to a patient or cell culture, alter homocysteine-induced gene regulation and/or the level of homocysteine or other sulfur-containing amino acids in the extracellular environment.

The methods and compositions of the invention will find use in the prophylaxis and treatment of various cardiovascular conditions, such as unstable angina, acute myocardial infarction (heart attack), cerebrovascular accidents (stroke), hypertension, renal artery stenosis, aortic stenosis, deep vein occlusive disease, and the like. The present invention is not limited to such uses, however, and the compositions and methods described herein may find use in other in vitro and in vivo situations whenever it is desirable to inhibit atherosclerotic plaque formation and accretion or to promote normal homeostasis of sulfur-containing amino acid metabolism.

A basis of the present invention is the use of subtractive hybridization of a population of cDNA species to selectively enrich for cDNA species which are preferentially expressed in cells subjected to elevated levels of extracellular homocysteine or other sulfur-containing amino acids or metabolites thereof. Another basis of the invention is a method using a polymerase-mediated chain extension, such as for example PCR, and differential amplification and/or display and/or recovery of reaction products, such as on a sequencing gel or otherwise, to effect isolation of cDNA species representing sequences of polynucleotide species, such as mRNA or primary or intermediate RNA transcripts, which are substantially increased or substantially decreased in abundance in mammalian cells exposed to hyperphysiological levels of homocysteine, such as occurs in patients having hyperhomocysteinemia. A variation of the method is used to identify mRNA species which exhibit an altered splicing pattern and/or mRNA length in the presence of hyperphysiological levels of homocysteine. The method is employed to isolate and identify cDNA species containing sequences of the mRNA species which typically encode mammalian proteins, such as, for example, a polypeptide which is induced or repressed by elevated levels of extracellular homocysteine.

In a broad aspect, the invention provides a method for identifying individual humans at risk for developing a atherosclerotic vascular disease, such as coronary artery disease, cerebral infarction, myocardial infarction, angina, unstable angina, hypertension, lower extremity phlebitis and deep vein thrombosis, and poor peripheral circulation, and related diseases causally related to atherosclerosis. The method comprises identifying individuals having elevated levels of serum homocysteine by determining the relative expression level of at least one homocysteine-regulated mRNA in a cellular sample (e.g., white blood cells or platelets isolated from peripheral blood) obtained from the individual; if the determination demonstrates that the relative expression level of the homocysteine-regulated mRNA is in a predetermined pathognomonic range, the individual is identified as a atherosclerosis disease candidate and a hyperhomocysteinemia candidate. Such disease candidates can be treated with therapies intended to reduce the level of serum homocysteine, which may include vitamin therapy and other modalities. The determination of the relative expression level of the homocysteine-regulated mRNA(s) is performed by a suitable diagnostic assay, which may include: (1) hybridization of an RNA sample of the sample to a polynucleotide probe of a predetermined sequence known to hybridize to said homocysteine-regulated mRNA, or (2) PCR, LCR, or other polynucleotide amplification method employing a primer or primer set of a predetermined sequence known to be capable of priming amplification of said homocysteine-regulated mRNA(s). Typically, the primer and probe sequences are obtained from a predetermined nucleotide sequence of an identified homocysteine-regulated mRNA or its cDNA. In an alternative embodiment, the determination of the relative expression level of the homocysteine-regulated mRNA(s) is performed by determining the level of an encoded protein product of the homocysteine-regulated mRNA(s), such as by immunoassay using an antibody predetermined to have a sufficient binding affinity and specificity to quantitatively assay the protein product.

Differential Display of cDNA

In an embodiment, the invention provides a method for identifying polynucleotides and polynucleotide sequences of mRNAs and the corresponding cDNAs which are substantially increased (i.e., at least 2-fold increased in relative abundance in the total mRNA pool) or substantially decreased (i.e., at least 50 percent decreased in relative abundance in the total mRNA pool) in cells exposed to hyperphysiological levels of homocysteine (e.g., 0.1 mM to about 5 mM for cultured endothelial or megakaryocytic cells) and/or cells explanted from an individual having transient or chronic hyperhomocysteinemia, as compared to cells exposed to normophysiological levels of homocysteine (e.g., less than 0.1 mM homocysteine in culture medium or cells explanted from an individual having serum homocysteine levels within one standard deviation of the population mean. The method generally involves obtaining a first mRNA sample which is obtained from cells exposed to hyperphysiological levels and obtaining a second mRNA sample from cells which are exposed to normophysiological levels of homocysteine; the first and second mRNA samples are individually subjected to PCR amplification with a 5' arbitrary primer(s) and, optionally, a 3' arbitrary primer(s) or an oligo(dT) 3' primer, under suitable reaction conditions whereby PCR amplification product(s) are labeled; the PCR amplification products are displayed by electrophoresis on a sequencing gel or other size-discriminatory separation method, and discrete size fractions (such as bands on a sequencing gel) of a desired type are identified by the presence and abundance of label in the fraction(s); fractions (e.g., bands on a gel) which are significantly increased or decreased in the sample of reactant products amplified from the mRNA sample obtained from cells exposed to a hyperphysiological homocysteine level relative to the sample obtained from cells exposed to normophysiological homocysteine levels are collected (such as by cutting out a portion of a sequencing gel corresponding to a band position) and the polynucleotide(s) are eluted and recovered. Often, multiple samples representing samples from cells exposed to varying levels of extracellular homocysteine (or exposure times) are amplified with the same arbitrary primers and the labeled reaction products run as one or more parallel lanes on said sequencing gel for comparison. Frequently, the recovered polynucleotides are amplified with PCR and/or cloned into a replicable vector and/or are sequenced. By this method, homocysteine-induced and homocysteine-repressed mRNA species are identified. Typically, the mRNA samples are obtained from cell types which are readily used for diagnostic assays and/or which are of the histological origin that is commonly involved in atherosclerotic disease (e.g., arterial intimal cells, smooth muscle cells, endothelial cells, fibroblasts, nucleated blood cells, and the like).

In an embodiment, mRNA or cDNA produced therefrom obtained separately from (1) a cell population exposed to elevated homocysteine levels and (2) a control cell population are amplified with PCR or a similar amplification method using one or more 5' arbitrary primers, either alone or in combination with a 3' poly(dT) primer or a 3' poly(dT) primer comprising 3' arbitrary nucleotide(s), typically two such 3' arbitrary nucleotide which are distinguishable from the poly(dT) tract as having the sequence $(dT)_zMN$, wherein z is typically about 10–20 (usually 11 to 15), M is dA, dC, or dG, and N is dA, dT, dC, or dG. Additional predetermined sequence may be present in the 5' portion of the 5' arbitrary primer and/or in the 5' portion of the 3' arbitrary primer (e.g., a restriction enzyme cutting site). Often, a series of parallel amplifications are conducted, each employing an aliquot or an equivalent of the mRNA or cDNA in conjunction with a subset (typically one) of a collection of 5' arbitrary primers in combination with a 3' poly(dT) primer or a subset (typically one) of a 3' poly(dT) primer comprising 3' arbitrary nucleotide(s). If desired, the sequences of the set of 5' arbitrary primers and the set of 3' arbitrary primers (if used) can be selected by the artisan such that while any given primer (or pair of primers) can prime the amplification of only a subpopulation of the mRNA or cDNA population, the entire set of primers is theoretically capable of collectively priming most or all of the species in the mRNA or cDNA population. Such a set of arbitrary primers capable of collectively priming amplification of at least a portion of substantially all species in the mRNA or cDNA population, while individually priming amplification of only a subpopulation, is referred to herein as a "coverage set" of arbitrary PCR primers. Often, arbitrary primers have typically one or two predetermined nucleotide at the 3' end, and which may include additional predetermined nucleotide at the 5' end (e.g., such as for a restriction site and/or to generate a clonable overlapping end).

Subtractive Libraries

In an embodiment of the invention, a subtraction cDNA library is used to identify mRNA sequences which are expressed in cells exposed to high levels of homocysteine and which are substantially not expressed or undetectable in control cells which are exposed to physiological levels of homocysteine or which are homocysteine-deficient. The subtracted cDNA library is produced by subtraction hybridization between: (1) a first cDNA population synthesized by reverse transcription of a mRNA sample from a first cell population and synthesis of second strand cDNA, and (2) a second cDNA population synthesized by reverse transcription and second strand synthesis of a mRNA sample from a second cell population, wherein said first cell population and said second cell population differ with regard to their exposure to homocysteine, typically by at least one order of magnitude or more, such that at least one RNA species is expressed in one cell population at a relative abundance which is at least two times, typically 10 times or more as abundant in the cellular RNA pool as compared to the other cell population. The subtractive hybridization procedure selectively removes said second cDNA population and DNA hybrids formed between one strand of a member of said first cDNA population and a complementary sequence in a member of said second cDNA population, thereby leaving a pool of subtracted cDNA enriched for sequences which are substantially more abundant in the first cDNA population than in the second cDNA population. Optionally, one or more additional cycles of subtractive hybridization are performed on the pool of subtracted cDNA. Separation of hybridized members of the first cDNA population from single-stranded or unhybridized double-stranded members of the first cDNA population can be accomplished by a variety of methods. Typically, the second cDNA population (also referred to as "driver cDNA") is labeled with a recoverable label, such as biotinyl or digoxigenyl groups, so that the pool of enriched driver cDNA is substantially derived from the first cDNA populations. Other means for removing driver cDNA and hybrids therewith can be used.

In an embodiment, the first cDNA population comprises an RNA species which is substantially absent or undetectable in said second cDNA population. For example but not limitation, the first cDNA population may comprise a cDNA containing a coding or noncoding sequence of an mRNA for a mammalian protein involved in metabolism of sulfur-containing amino acids or other metabolic or structural function, wherein the second cDNA population may substantially lack such mRNA specie(s). Subtractive hybridization can be performed in a hybridization reaction between the first cDNA population and the second cDNA population, typically wherein the second cDNA population comprises a recoverable label such as a covalently attached biotinyl substitutent or the like. Selective removal of driver/tester cDNA hybrids and unhybridized driver cDNA from the hybridization reaction is accomplished, such as by contacting the hybridization reaction (cDNA molecules) with a ligand which binds to the recoverable label present on the driver cDNA (e.g., avidin, streptavidin, anti-biotin antibody, etc.) and can be selectively removed from the hybridization reaction, thereby substantially enriching the remaining hybridization reaction for the subtracted cDNA derived from the first (tester) cDNA population. One or more additional cycles of subtractive hybridization can be performed on the subtracted cDNA; typically against the second cDNA population (recursive subtractive hybridization) and/or a third (or subsequent) cDNA population wherein said RNA species is substantially absent or undetectable; usually wherein the second, third or subsequent cDNA population comprises a recoverable label.

In an embodiment, the first cDNA population is obtained by reverse transcription of RNA obtained from a first cell population comprising mammalian cells exposed to elevated homocysteine or other sulfur-containing amino acid(s), and a second cDNA population is obtained by reverse transcription of RNA obtained from a second cell population comprising mammalian cells which are exposed to physiological conditions (e.g., levels of homocysteine and other sulfur-containing amino acids which are within one standard deviation of the population mean for humans). Typically, the first and second cell populations are of the same or equivalent histological type (e.g., fibroblast, epithelial, endothelial, smooth muscle, macrophage, megakaryocyte, lymphocyte, etc.) to reduce the number of RNA species which are differentially expressed. Where a third (or subsequent) cDNA population is employed, it is generally obtained by reverse transcription of RNA from a cell population of mammalian cells which are histologically similar or distinct from the first cell population and which are similar or identical conditions.

Polynucleotides Induced or Repressed by Homocysteine

The present invention relates to the unexpected discovery that exposure of human cells to hyperphysiological levels of homocysteine produces a substantial increase or reduction in the relative abundance of particular mRNA species, especially in histological types of cells which are present in the vasculature (e.g., endothelial cells) or circulatory system (e.g., nucleated cells of a hemopoietic lineage).

In an embodiment, the invention provides polynucleotides obtained by the disclosed method, wherein the polynucleotides comprise partial or full-length cDNA sequences of mRNA species which are induced (i.e., the relative abundance of the species in the mRNA pool is increased) at least 2-fold, typically by at least an order of magnitude, by the presence of hyperphysiological homocysteine (e.g., about 5 mM homocysteine in cell culture) or which are repressed (i.e., the relative abundance of the species in the mRNA pool is decreased) by more than about 50 percent, typically by at least an order of magnitude (90 percent), or more. The invention also provides the use of these polynucleotides for diagnosis of homocysteinemia and/or atherosclerotic disease, therapeutic monitoring, pharmaceutical development and testing, and treatment of homocysteinemia and vascular disease or a predisposition thereto.

The invention also provides expressed sequence tags (ESTs) and polynucleotide sequences of mRNA species which are substantially increased or substantially decreased in relative abundance in cells exposed to hyperphysiological levels of homocysteine. The ESTs are typically at least about 25 nucleotides long, often at least 35 nucleotides long, and frequently are at least 100 nucleotides long or longer up to a full-length mRNA which may comprise 300 to several thousand nucleotides.

The invention provides polynucleotides comprising a sequence of at least 25 consecutive nucleotides which is identical to or complementary to portion of an mRNA species which is induced or repressed by homocysteine or other sulfur-containing amino acids; the mRNA species may encode a functional protein, although the polynucleotide sequence of the invention may comprise or consist of a non-coding sequence.

In an embodiment, the invention provides a polynucleotide comprising a substantially full-length cDNA sequence identical to or complementary to a mammalian mRNA species which is substantially increased or substantially decreased in relative abundance in cells exposed to hyperphysiological levels of sulfur-containing amino acids, such as homocysteine, referred to hereafter as "homocysteine-regulated genes", of which dhc-1 (FIG. 5) is an example. In one aspect, the polynucleotide comprises a sequence which is substantially identical, identical, substantially complementary, or complementary to least 30 consecutive nucleotide of the sequence designated dhc-1 and shown in FIG. 5. The invention also provides a full-length dhc-1 cDNA and gene sequence obtained from a mammal, preferably a human. Accordingly, an embodiment of the invention involves the formation of a purified and/or isolated mammalian dhc-1 cDNA and genomic gene and fragments thereof.

Polynucleotide sequences encoding dhc-1 polypeptides are provided. Polynucleotides comprising these sequences can serve as templates for the recombinant expression of quantities of dhc-1 polypeptides, such as full-length mammalian dhc-1 or immunogenic fragments thereof. Many polynucleotides comprising these sequences can also serve as probes for nucleic acid hybridization to detect the transcription rate and mRNA abundance of dhc-1 mRNA in individual cells (e.g., lymphocytes or other somatic or germ cell types) by in situ hybridization and the like, and in specific cell populations by Northern blot analysis and/or by in situ hybridization (Alwine et al.(1977) *Proc. Natl. Acad. Sci. U.S.A.* 74: 5350) and/or PCR amplification and/or LCR detection, or other suitable amplification method.

Polynucleotides comprising sequences encoding dhc-1 amino acid sequences can serve as templates for the recombinant expression of quantities of dhc-1 polypeptides, such as human dhc-1 and murine dhc-1.

The invention also provides host cells expressing dhc-1 polypeptides encoded by a polynucleotide other than a naturally-occurring dhc-1 gene or homolog gene of the host cell (if present).

The invention also provides antisense polynucleotides complementary to polynucleotides encoding dhc-1 polypeptide sequences, or non-coding portions thereof. Such antisense polynucleotides are employed to inhibit transcription and/or translation of the dhc-1 mRNA species and thereby effect a reduction in the amount of the respective dhc-1 polypeptide in a cell (e.g., an endothelial or nucleated blood cell of a patient). Such antisense polynucleotides can function as dhc-1-modulating agents by inhibiting dhc-1 expression. The dhc-1 antisense polynucleotides are substantially identical to at least 25 contiguous nucleotides of the complementary sequence of the dhc-1 cDNA sequence shown in FIG. 5 and denoted SEQ ID NO: 5. The dhc-1 antisense polynucleotides are typically ssDNA, ssRNA, methylphosphonate backbone nucleic acids, phosphorothiolate backbone, polyamide nucleic acids, and the like antisense structures known in the art. In one aspect of the invention, an antisense polynucleotide is administered to inhibit transcription and/or translation of dhc-1 in a cell.

In a variation of the invention, polynucleotides of the invention are employed for diagnosis of pathological conditions or genetic disease that involve homocysteinemia, atherosclerosis, or other medical conditions related to the condition of hyperhomocysteinemia or to a homocysteine-regulated gene, such as dhc-1, and more specifically conditions and diseases that involve alterations in the structure or abundance of a homocysteine-regulated gene product (e.g., dhc-1) polypeptide, RNA transcript or splicing intermediate, mRNA, or genomic gene locus.

The invention also provides antibodies which bind to dhc-1 with an affinity of about at least $1 \times 10^7$ $M^{-1}$ and which lack specific high affinity binding for most other polypeptides. Such antibodies can be used as diagnostic reagents to identify cells exhibiting altered dhc-1 function (e.g., increased dhc-1 expression) in a cellular sample from a patient (e.g., a lymphocyte or megakaryocte-containing blood sample, a solid tissue biopsy, and endothelial cell explant), as commercial reagents to identify, isolate, and/or quantitate dhc-1 polypeptides in samples and histological specimens, and the like. Samples having cells with a substantially increased relative amount of dhc-1 protein as compared to a control (or standardized) cell population of the same cell type(s), are pathognomonic for hyperhomocysteinemia and a predisposition to atherosclerosis. Frequently, anti-dhc-1 antibodies are included as diagnostic reagents for immunohistopathology staining of cellular samples in situ, such as histological sections comprising vasculature (e.g., endothelial cells and intima in small arterioles or capillaries.

The invention also involves the use of the protein dhc-1 or mutein or fragment thereof for performing immunochemical methods for the detection and determination of the protein, in order to monitor therapy to reduce homocysteine levels or to detect or monitor the course of disease (e.g., hyperhomocysteinemia and/or atherosclerosis or other vascular disease).

The invention also provides dhc-1 polynucleotide probes for diagnosis of disease states (e.g., hyperhomocysteinemia or atherosclerosis predisposition) by detection of substantially elevated dhc-1 mRNA levels in cells explanted from a patient, or detection of a pathognomonic dhc-1 allele (e.g., by RFLP or allele-specific PCR analysis) linked to a genetic disease or predisposition. Typically, the detection will be by in situ hybridization using a labeled (e.g., $^{32}P$, $^{35}S$, $^{14}C$, $^3H$, fluorescent, biotinylated, digoxigeninylated) dhc-1 polynucleotide, although Northern or Southern blotting, dot blotting, or solution hybridization on bulk genomic DNA, RNA, or poly $A^+$ RNA isolated from a cell sample may be used, as may PCR amplification using dhc-1-specific primers. Test samples containing cells which contain a substantially increased amount of dhc-1 mRNA as compared to cells of the same cell type(s) from a comparable sample from a normal individual (or standardized normal value) identify the individual from which the test sample was obtained as a disease candidate for homocysteinemia and atherosclerosis predisposition. Similarly, the detection of pathognomonic rearrangements, deletion, or amplification of the dhc-1 gene locus or closely linked loci in a cell sample will identify the presence of a pathological condition or a predisposition to developing a pathological condition (e.g., cancer, genetic disease) linked to the dhc-1 locus. The polynucleotide probes are also used for forensic identification of individuals, such as for paternity testing or identification of criminal suspects or unknown decedents.

The present invention also provides a method for diagnosing a homocysteine-related disease (e.g., homocysteinemia, atherosclerosis) in a human patient, wherein a diagnostic assay (e.g., immunohistochemical staining of fixed cells by an antibody that specifically binds dhc-1 polypeptides) is used to determine if a predetermined pathognomonic concentration of dhc-1 polypeptide or its encoding mRNA is present in a biological sample from a human patient; if the assay indicates the presence of dhc-1 polypeptide or its encoding mRNA outside of the normal range (e.g., outside the predetermined pathognomonic concentration range), the patient is diagnosed as having a disease condition or predisposition to developing premature atherosclerosis.

The invention provides a composition for diagnosing a homocysteine-related pathological condition, comprising a polynucleotide probe comprising at least 25 nucleotide which are substantially identical to a dhc-1 gene sequence, typically at least 35 nucleotide which are substantially identical to dhc-1. In an aspect, the polynucleotide probe is labeled. In an aspect, the polynucleotide probe is immobilized, such as on a solid substrate or DNA probe array. In an aspect, the dhc-1 polynucleotide is used as a primer for PCR amplification, often in conjunction with a second (reverse) primer which may be a dhc-1 polynucleotide, an oligo(dT) primer, a randomer or mixture of randomers or nested set of promiscuous primers, or the like; however, some variations may employ spontaneous self-priming via hairpin loop formation in the absence of a second primer.

In a broad aspect, the invention provides a method for identifying individuals having an increased risk for developing premature atherosclerosis, the method comprising determining the relative abundance of a homocysteine-regulated mRNA in a cellular sample obtained from an individual as compared to a predetermined standard value and/or as compared to a cellular sample obtained from one or more normal individuals predetermined to have serum homocysteine levels within one standard deviation of the population mean value. Cellular samples having a relative abundance of said homocysteine-regulated gene which is in a predetermined pathognomonic range are thereby identified as hyperhomocysteinemia candidates and/or atherosclerosis candidates.

In an embodiment, the present invention provides methods for detecting and quantifying a concentration of a homocysteine-regulated mRNA or protein species in biological samples, such as a cellular sample of a biological fluid (e.g., nucleated blood cells) or a tissue biopsy sample (e.g., buccal epithelium, vascular intimal cells).

It is a further object of the invention to provide methods for developing diagnostic methods and diagnostic kits for determining the concentration of a homocysteine-regulated mRNA or protein in cells of a biological sample. These methods and kits will typically comprise a polynucleotide comprising a sequence of at least 25 nucleotide which are substantially identical or complementary to a homocysteine-regulated mRNA, and/or an antibody which is specifically reactive with a protein encoded by a homocysteine-regulated gene.

The present invention also provides a method for diagnosing hyperhomocysteinemia and/or a predisposition to early development of atherosclerosis in a human patient, wherein a diagnostic assay is used to determine if a predetermined pathognomonic concentration of a homocysteine-regulated mRNA is present in a cells of a biological sample from a human patient; if the assay indicates the presence of a homocysteine-regulated mRNA sufficiently above or below a predetermined pathognomonic concentration range, the patient is diagnosed as an disease candidate. Modifications of the method are provided which adapt the diagnostic assay for use in the diagnosis of human pathological conditions other than hyperhomocysteinemia. A diagnosis of hyperhomocysteinemia is a presumption of an increased risk for premature development of vascular disease, such as atherosclerosis.

In one aspect, the invention provides a polynucleotide (e.g., as a primer or probe) which specifically hybridizes to a predetermined homocysteine-regulated mRNA, wherein the polynucleotide is affixed to a solid substrate, typically wherein the solid substrate has a plurality of polynucleotide species affixed thereto, in a spatially defined array whereby each cell typically contains a single polynucleotide species, with the array often comprising in excess of 1000 distinct polynucleotide species. The probe polynucleotide is typically affixed by covalent linkage to the solid substrate. The solid substrate constitutes an array of polynucleotide probes and/or primers, wherein at least one member of the array is a probe polynucleotide for a predetermined homocysteine-regulated mRNA. Generally, the solid substrate will be less than 10 cm$^3$ and comprise at least 1024 positionally distinct polynucleotide species, at least one of which is a probe polynucleotide which binds to a predetermined homocysteine-regulated mRNA. Such polynucleotides arrays on solid substrates (e.g., a polysilicon wafer) can be used for genotype determination, disease detection and diagnosis, therapeutic efficacy monitoring, forensic identification, or for sequencing (e.g., of a pool containing unknown polynucleotides; for sequencing a mammalian genome or cDNA library), or other like uses.

The invention provides a diagnostic kit for detecting a pathological condition, such as atherosclerosis and hyperhomocysteinemia, wherein the kit contains at least one polynucleotide predetermined to hybridize to a homocysteine-regulated mRNA or to prime amplification of a homocysteine-regulated mRNA.

The invention provides a gene therapy method and compositions therefor, comprising a polynucleotide comprising a sequence of a predetermined homocysteine-regulated mRNA, which can often be operably linked to polynucleotide sequences to drive expression (e.g., promoter, enhancer, etc.) or other components of a gene therapy vector or homologous recombination construct, according to method and materials known in the art. One variation comprises a polynucleotide in a viral vector for gene therapy. A variation employs a polynucleotide in a gene therapy delivery formulation (e.g., comprising cationic or neutral lipids, polylysine, polyarginine, or other delivery-enhancing vehicle); the polynucleotide comprising the homocysteine-regulated gene sequence may be formulated with other polynucleotides for therapeutic benefit.

The invention also provides the use of a polynucleotide comprising a sequence of a homocysteine-regulated mRNA or gene to diagnose and/or treat disease, or to identify an individual based, in part, on their genotype as defined by a allele-specific restriction site pattern or nucleotide sequence, or abundance of mRNA transcripts or RNA splicing pattern variation.

The invention also provide methods for isolating genomic gene clones of homocysteine-regulated mammalian genes. Such clones can include transcriptional regulatory sequences, such as promoters, enhancers, silencers, and the like; and often can include a sequence or portion which confers transcriptional responsiveness to the level of extracellular homocysteine (i.e., a "homocysteine response element"), preferably in a dose-dependent manner.

The invention provides screening assays for identifying agents which modulate expression of genes which are regulated by the level of extracellular homocysteine. The screening assays can employ a variety of reporter strategies. In one embodiment, the relative abundance of at least one homocysteine-regulated mRNA is determined in a cell culture or cellular sample from a whole animal in the presence of and, separately, in the absence of an added agent; agents which produce a substantial change in the relative abundance of said homocysteine-regulated. mRNA are thereby identified as candidate pharmaceutical for modifying a pathological condition or disease predisposition, such as hyperhomocysteinemia and/or atherosclerosis. Typically, the assay is performed using cells which are cultured in a culture medium having at least 0.1 mM homocysteine, often having at least 1 mM to about 5 mM homocysteine.

In one embodiment, candidate therapeutic agents are identified by their ability to inhibit homocysteine-induced transcription of a homocysteine-regulated gene with minimal or undetectable inhibition of other genes, such as GAPDH, which are not substantially regulated by extracellular homocysteine levels. Preferably, the inhibition of an active agent is dose-dependent, and dose-dependent transcriptional modulating agents are preferably selected.

The invention provides for the use of homocysteine-regulated polypeptides, homocysteine-regulated polynucleotides, and sequences thereof, for diagnosis and treatment of disease, for screening compound banks to identify candidate pharmaceutical agents, and for development of transgenic or knockout mice having an altered genotype and optionally an altered phenotype.

BRIEF DESCRIPTION OF THE DRAWINGS

FIGS. 5A–5B (SEQ ID NOS:5–6). Partial nucleotide sequence of the dhc-1 cDNA fragment (designated T7MGAP1B.SEQ) shown in panel A. Using the GenBank DNA database, dhc-1 was shown to be >96% identical to the unidentified human EST designated HHCJ64 (panel B).

DETAILED DESCRIPTION

Figure 1:
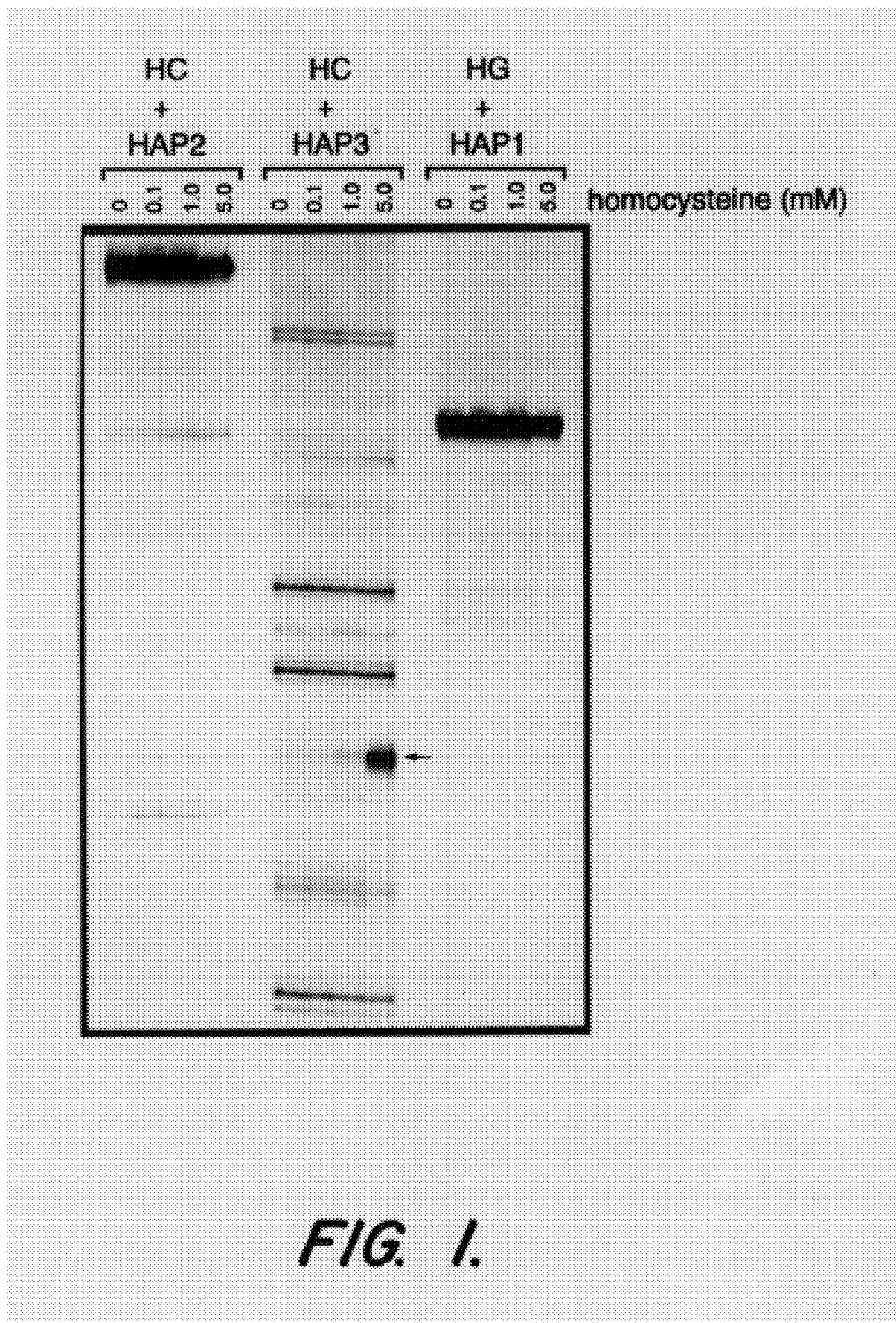
FIG. 1. Identification of a homocysteine-inducible gene by mRNA differential display. Total RNA from HUVECs treated for 18 hr with 0, 0.1, 1.0 or 5.0 mM homocysteine were DNase-treated and subjected to mRNA differential display. The radiolabelled cDNA fragments were then resolved on 6% sequencing gels. A candidate cDNA fragment which demonstrates dose-dependent upregulation in the presence of homocysteine is marked by an arrow. HC, anchor primer (SEQ ID NO:7) 5'-AAGCT$_{(11)}$C-3'. HG, anchor primer (SEQ ID NO:8) 5'-AAGCT$_{(11)}$G-3'. HAP1-3, arbitrary primers (SEQ ID NOS:1–3) 5'-AAGCTTGATTGCC-3', 5'-AAGCTTCGACTGT-3' and 5'-AAGCTTTGGTCAG-3', respectively.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

Definitions

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference).

Unless specified otherwise, the conventional notation used herein portrays polynucleotides as follows: the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

As used herein, the term "polynucleotide" refers to a polymer composed of a multiplicity of nucleotide units (ribonucleotide or deoxyribonucleotide or related structural variants) linked via phosphodiester bonds. A polynucleotide can be of substantially any length, typically from about 10 nucleotide to about 1×10$^9$ nucleotide or larger. As used herein, an "oligonucleotide" is defined as a polynucleotide of from 6 to 100 nucleotide in length. Thus, an oligonucleotide is a subset of polynucleotides.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "corresponds to" is used herein to mean that a polynucleotide sequence is homologous (i.e., is identical, not strictly evolutionarily related) to all or a portion of a reference polynucleotide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 12 nucleotide in length, frequently at least 15 to 18 nucleotide in length, and often at least 25 nucleotide in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 12 contiguous nucleotide positions wherein a polynucleotide sequence may be compared to a reference sequence of at least 12 contiguous nucleotide and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25–50 nucleotide, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotide and an agent for polymerization such as DNA polymerase and at a suitable temperature and pH. The primer is preferably single-stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence, the oligonucleotide primer typically contains 15–25 or more nucleotides, although it may contain fewer nucleotides. Short primer molecules generally require lower temperatures to form sufficiently stable hybrid complexes with their templates. In some embodiments, the primers can be large polynucleotides, such as from about 200 nucleotide to several kilobases or more. The primers herein are selected to be substantially complementary to the different strands of each specific sequence to be amplified. The primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to be amplified to hybridize therewith and thereby form a template for synthesis of the extension product of the other primer.

As used herein, "suitable reaction conditions" are those conditions suitable for conducting PCR amplification using conventional reagents. Such conditions are known or readily established by those of skill in the art, and can be exemplified by the reaction conditions used in U.S. Pat. Nos. 4,683,202, 4,683,195, and 4,800,159, which are incorporated herein by reference. As one example and not to limit the invention, suitable reaction conditions can comprise: 0.2 mM each dNTP, 2.2 mm $MgCl_2$, 50 mM KCl, 10 mM Tris-HCl pH 9.0, 0.1% Triton X-100.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for PCR and many polynucleotide enzymatic reactions and manipulations are generally physiological conditions. In general, in vitro physiological conditions comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions and/or antifoam agents and/or scintillants.

As used herein, the terms "label" or "labeled" refers to incorporation of a detectable marker, e.g., by incorporation of a radiolabeled nucleotide or incorporation of nucleotide having biotinyl moieties that can be detected by marked avidin (e.g., streptavidin containing a fluorescent marker or enzymatic activity that can be detected by optical or calorimetric methods). Various methods of labeling polynucleotides are known in the art and may be used. Examples of labels include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, and the like. In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "recombinant" used herein refers to macromolecules produced by recombinant DNA techniques wherein the gene coding for a polypeptide is cloned by known recombinant DNA technology. For example, an amplified or assembled product polynucleotide may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host. Alternatively, the product polynucleotide may serve a non-coding function (e.g., promoter, origin of replication, ribosome-binding site, etc.).

As used herein "normal blood" or "normal human blood" refers to blood from a healthy human individual who does not have active coronary artery disease, atherosclerotic disease, or other vascular disorder, or an identified predisposition for developing a vascular disease; such individuals have serum homocysteine levels within or below the normal range for the age-adjusted population and exhibit typical metabolic response to methionine overloading; such individuals are typically normotensive and can be identified by various means, including coronary arterial scans, and the like. Similarly, "normal serum", "normal plasma", "normal urine", and "normal saliva" refer to the respective fluids obtained from a healthy human individual who does not have active atherosclerotic disease, homocysteinemia, or other identified condition associated with a vascular pathological disorder.

As used herein "pathognomonic concentration" refers to a concentration of an analyte in a sample, for example the concentration of a protein in a blood, plasma, serum, urine, or saliva sample, or a concentration of a protein or mRNA in a cell (e.g., nucleated cell of a hematopoietic lineage) of a cellular sample obtained from an individual, wherein the concentration of the analyte is indicative of the presence of a specific disease or a predisposition to developing a specific disease, such as atherosclerotic disease and/or homocysteinemia. A pathognomonic concentration is a concentration of an analyte that falls outside the range of normal clinical values that is established by prospective and/or retrospective statistical clinical studies. Generally, an individual having an atherosclerotic disease (e.g., coronary or carotid artery lumen narrowing) and/or clinical hyperhomocysteinemia will exhibit a concentration of the analyte in a tissue or biological fluid sample that is higher than the range of concentrations that characterize normal, undiseased individuals; typically the pathognomonic concentration is at least about one standard deviation above the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional. Most typically the analyte is a protein or mRNA expressed in a nucleated blood cell, endothelial cell, or vascular smooth muscle or fibroblastic cell, wherein the abundance of the protein or mRNA species is elevated or reduced by at least one standard deviation from the established mean population value by the presence of elevated levels of homocysteine characteristic of homocysteinemia.

As used herein, the term "reporter polynucleotide" refers to a polynucleotide sequence comprising a transcriptional regulatory sequence operably linked to a structural sequence encoding a reporter protein (e.g., β-galactosidase, luciferase, chloramphenicol acetyltransferase, green fluorescent protein). Preferred transcriptional regulatory sequences are obtained from the promoter region and 5' flanking region of homocysteine-regulated genes.

The term "transcriptional modulation" is used herein to refer to the capacity to either enhance transcription or inhibit transcription of a structural sequence linked in cis; such enhancement or inhibition may be contingent on the occurrence of a specific event, such as stimulation with an inducer (e.g., homocysteine) and/or may only be manifest in certain cell types (e.g., enothelial cells, nucleated blood cells). The altered ability to modulate transcriptional enhancement or inhibition may affect the inducible transcription of a gene, or may effect the basal level transcription of a gene, or both. For example, a reporter polynucleotide may comprise a homocysteine-inducible enhancer-promoter driving transcription of a sequence encoding a reporter protein. Such a reporter polypeptide may be transferred to a homocysteine-responsive cell line for use as a reporter host cell to screen a cDNA expression library for cloned sequences that affect homocysteine-induced transcriptional modulation. Cloned sequences that enhance transcription of the reporter in the absence of homocysteine may be identified as putative positive regulators of homocysteine-response elements, whereas cloned sequences that silence expression of the reporter in cells cultured in the presence of homocysteine may be identified (e.g., by selecting cells not expressing the reporter) as sequences encoding proteins that interfere with the expression of homocysteine-responsive genes. Numerous other specific examples of transcription regulatory elements, such as specific enhancers and silencers, are known to those of skill in the art and may be selected for use in the methods and polynucleotide constructs of the invention on the basis of the practitioner's desired application. Literature sources and published patent documents, as well as GenBank™ and other sequence information data sources can be consulted by those of skill in the art in selecting suitable transcription regulatory elements for use in the invention. Where necessary, a transcription regulatory element may be constructed by synthesis (and ligation, if necessary) of oligonucleotides made on the basis of available sequence information.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, a "homocysteine-regulated mRNA" or "homocysteine-responsive mRNA" is a mRNA species which is at least 2-fold increased in relative abundance in the total mRNA pool or at least 50 percent decreased in relative abundance in the total mRNA pool in cells exposed to hyperphysiological levels of homocysteine (e.g., 1 mM to about 5 mM for cultured endothelial or megakaryocytic cells) and/or cells explanted from an individual having transient or chronic hyperhomocysteinemia.

DESCRIPTION OF THE PREFERRED EMBODIMENTS

Generally, the nomenclature used hereafter and many of the laboratory procedures in cell culture, molecular genetics, and nucleic acid chemistry and hybridization described below are those well known and commonly employed in the art. Standard techniques are used for recombinant nucleic acid methods, polynucleotide synthesis, in vitro polypeptide synthesis, and the like and microbial culture and transformation (e.g., electroporation). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.; each of which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer. The polynucleotide primers may be prepared using any suitable method, such as, for example, the phosphotriester and phosphodiester methods, or automated embodiments thereof. In one such automated embodiment diethylphosphoramidites are used as starting materials and may be synthesized as described by Beaucage et al. (1981) *Tetrahedron Letters* 22: 1859. One method for synthesizing oligonucleotides on a modified solid support is described in U.S. Pat. No. 4,458,066. It is also possible to use a primer which has been isolated from a biological source (such as a restriction endonuclease digest or the like.

Methods for PCR amplification are described in the art (*PCR Technology: Principles and Applications for DNA Amplification* ed. H A Erlich, Stockton Press, New York, N.Y. (1989); *PCR Protocols: A Guide to Methods and Applications*, eds; Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; and U.S. Pat. Nos. 4,683,202 and 4,965,188, each of which are incorporated herein by reference) and exemplified hereinbelow.

It is evident that optimal PCR and hybridization conditions will vary depending upon the sequence composition and length(s) of the targeting polynucleotide(s) and target(s), and the experimental method selected by the practitioner. Various guidelines may be used to select appropriate primer sequences and hybridization conditions (see, Maniatis et al., *Molecular Cloning: A Laboratory Manual* (1989), 2nd Ed., Cold Spring Harbor, N.Y.; Berger and Kimmel, *Methods in Enzymology, Volume* 152, *Guide to Molecular Cloning Techniques* (1987), Academic Press, Inc., San Diego, Calif.; *PCR Protocols: A Guide to Methods and Applications*, eds. Innis, Gelf land, Snisky, and White, Academic Press, San Diego, Calif. (1990); Benton W D and Davis R W (1977) *Science* 196: 180; Goodspeed et al. (1989) *Gene* 76: 1; Dunn et al. (1989) *J. Biol. Chem.* 264: 13057 which are incorporated herein by reference.

Overview

Mounting evidence has shown that elevated blood levels of homocysteine represents an independent risk factor for vascular disease. Presently, however, there is no simple and/or reliable test to determine individuals with hyperhomocysteinemia. In addition, there is no strategy to measure the success of presently available treatments which lower blood homocysteine-levels.

The invention discloses an approach to identify homocysteine-induced genes for the successful diagnosis and treatment of vascular disease. By identifying these genes and their gene products we will be able to better understand the mechanisms involved in homocysteine-induced vascular disease so that rational strategies for the detection and prevention of hyperhomocysteinemia can be pursued.

The invention discloses a method which employs mRNA differential display (Liang and Pardee, (1992) *Science* 257: 967; Liang et al. (1993) *Nucleic Acids Res.* 21: 3269 to identify specific homocysteine-induced genes. The identification of these genes provides a direct insight into the cytotoxic effect of homocysteine, thus leading to new strategies in the detection and prevention of homocysteine-induced vascular disease and thrombosis.

A basis of the present invention is the use of differential display, comprising (1) obtaining two mRNA populations wherein a first mRNA population represents mRNA species expressed in cells exposed to elevated levels of homocysteine or obtained directly from hyperhomocysteinemia patients, and a second mRNA population represents mRNA species expressed in the same type of cells cultured with physiological levels of homocysteine or deficient in homocysteine or obtained directly from a normal patient having a homocysteine level at or below the population mean, and (2) PCR amplification, under suitable PCR conditions, of said mRNA populations with a 5' primer of arbitrary nucleotide sequence and optionally with a 3' primer comprising poly(dT) and/or poly(dT) and two or more arbitrary nucleotide at the 3' end to generate PCR products, and (3) differential display of said PCR products on an electrophoretic gel and recovery of individual species of said PCR products by recovery from the gel, wherein the recovered species are identified as homocysteine-regulated mRNA sequences based on differential expression levels shown by distinct signal intensity on the gel.

In a specific embodiment, the method is used to isolate and identify polynucleotides having sequences complementary to or corresponding to a coding or non-coding portion of a naturally occurring mRNA which is increased more than 2-fold in relative abundance in the total mRNA pool in cells exposed to conditions of elevated homocysteine as compared to cells exposed to conditions of physiological concentrations or subphysiological concentrations of homocysteine.

Subtractive hybridization can be useful for enriching a pool of up-regulated cDNA species from mRNA expressed in cells exposed to hyperphysiological homocysteine, and conventional screening of the resultant library(ies) will identify up-regulated mRNA species in the selected cDNA pool.

Differential Display of Amplified Products

The general strategy is to amplify partial cDNA sequences from subsets of species in the mRNA pool obtained from cells exposed to elevated homocysteine levels and separately from the mRNA pool obtained from cells exposed to normal homocysteine levels, by PCR (RT-PCR) amplification (or other amplification means) using one or a series of arbitrary sequence primers. Arbitrary primers are selected according to various criteria at the discretion of the practitioner so that each will amplify only a fraction of the species in the mRNA pool so that the amplification products can be resolved and individually recovered on a separation system, such as a polyacrylamide gel (e.g., a DNA sequencing PAGE format).

In part because the number and complexity of mRNA species represented in any particular mRNA pool may vary considerably depending upon the nature and complexity of the cell type(s) and culture conditions, the selection of arbitrary primers and their sequence(s) are determined by the practitioner with reference to the literature (see, Liang and Pardee (1992) *Science* 257: 967; Liang et al. (1992) *Cancer Res.* 52: 6966; Liang et al. (1993) *Nucleic Acids Res.* 21: 3269; Utans et al. (1994) *Proc. Natl. Acad. Sci. (U.S.A.)* 91: 6463; Zimmermann et al. (1994) *Proc. Natl. Acad. Sci. (U.S.A.)* 91: 5456; Wang and Brown (1991) *Proc Natl Acad Sci U S A* 88: 11505; Fischer et al. (1995) *Proc. Natl. Acad. Sci. (U.S.A.)* 92: 5331; Lohmann et al. (1995) *Biotechniques* 18: 200; Reeves et al. (1995) *Biotechniques* 18: 18; Maser et al. (1995) *Semin Nephrol* 15: 29; Chen et al. (1994) *Biotechniques* 16: 1002; Callard et al. (1994) *Biotechniques* 16: 1096; and Mou et al. (1994) *Biochem Biophys Res Commun* 199: 564, incorporated herein by reference).

The mRNA pool is amplified with suitable arbitrary primer(s) (i.e., primer having a predetermined sequence which is selected without reference to a sequence of a desired differentially expressed mRNA; as described in Liang and Pardee (1992) op. cit) for a suitable number of amplification cycles to generate sufficient amplification product for display and recovery of desired species; this can be determined empirically by the practitioner. The primer(s) may comprise 5'-terminal sequences which serve to anchor other PCR primers (distal primers) and/or which comprise a restriction site or half-site or other ligatable end. The amplified products are usually labeled and are typically are resolved by electrophoresis on a polyacrylamide gel; the location(s) where label is present are excised and the labeled product species is/are recovered from the gel portion, typically by elution. The resultant recovered product species (ESTs) can be subcloned into a replicable vector with or without attachment of linkers, amplified further, and/or sequenced directly.

Subtractive Hybridization

An alternative approach is to use subtractive hybridization, wherein RNA prepared by conventional methods from a first cell population and RNA from a second cell population are separately reverse-transcribed and second-strand synthesized to form two pools of double-stranded cDNA, a tester pool comprising sequences of the mRNA species(s) desired to be enriched for, and a driver pool comprising the sequences desired to be subtracted from the tester pool. The two pools may be fragmented by endonuclease digestion (restriction endonuclease or non-specific endonuclease) if desired to enhance hybridization efficiency. The driver pool is labeled, such as by photobiotinylation or attachment of another suitable recoverable label. The driver pool and tester pool are denatured and mixed together in a reaction mixture under hybridization conditions and incubated for a suitable hybridization period. The reaction mixture is contacted with a ligand which binds the recoverable label on the driver cDNA and which can be readily recovered from the reaction mixture (e.g., avidin attached to magnetic beads), such that a substantial fraction of the driver cDNA and any tester cDNA hybridized thereto is selectively removed from the reaction mixture. The remaining reaction mixture is enriched for tester cDNA species which are preferentially expressed in the first cell population as compared to the second cell population. The enriched (subtracted) tester cDNA pool may be subjected to one or more additional rounds of subtractive hybridization with a pool of labeled driver cDNA, which may be substantially identical to the initial pool of driver cDNA or which may represent a different cell population having mRNA species which are desired to be subtracted from the subtracted tester cDNA pool. A variety of means for accomplishing the subtractive hybridization(s) and suitable methodological guidance are available to the artisan (see, Lee et al. (1991) *Proc. Natl. Acad. Sci. (U.S.A.)* 88: 2825; Milner et al. (1995) *Nucleic Acids Res.* 23: 176; Luqmani et al. (1994) *Anal. Biochem.* 222: 102; Zebrowski et al. (1994) *Anal. Biochem.* 222: 285; Robertson et al. (1994) *Genomics* 23: 42; Rosenberg et al. (1994) *Proc. Natl. Acad. Sci. (U.S.A.)* 91: 6113; Li et al. (1994) *Biotechniques* 16: 722; Hakvoort et al. (1994) *Nucleic Acids Res.* 22: 878; Satoh et al. (1994) *Mutat. Res.* 316: 25; Austruy et al. (1993) op.cit; Marechal et al. (1993) *Anal. Biochem.* 208: 330; El-Deiry et al. (1993) *Cell* 75: 817; Hara et al. (1991) *Nucleic Acids Res.* 19: 7097; and Herfort and Garber (1991) *Biotechniques* 11: 598, each incorporated herein by reference). cDNA species remaining in the tester pool can be cloned, amplified, and/or sequenced for unambiguous identification, such as in the form of an EST sequence.

Full-Length cDNA

Once the EST(s) are recovered, they may be used to obtain a substantially full-length cDNA from a cDNA library. The EST(s) can be sequenced and the sequence information used to generate a primer for primer extension (5'-RACE technique) or the EST can be labeled and used as a hybridization probe to identify larger cDNA clones from a cDNA library.

Genomic or cDNA clones of the subtracted cDNA species may be isolated from clone libraries (e.g., available from Clontech, Palo Alto, Calif.) using the labeled EST (e.g., by nick-translation or end-labeling) or using hybridization probes designed on the basis of the nucleotide sequences identified and using conventional hybridization screening methods (e.g., Benton W D and Davis R W (1977) *Science* 196: 180; Goodspeed et al. (1989) *Gene* 76: 1). Where a full-length cDNA clone is desired, clone libraries containing cDNA derived from somatic cell mRNA. Alternatively, synthetic polynucleotide sequences corresponding to all or part of the EST sequences may be constructed by chemical synthesis of oligonucleotides. Additionally, polymerase chain reaction (PCR) using primers based on the sequence data disclosed in the EST sequences may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the EST sequence data and a second primer that is not based on that sequence data may be used.

Disclosure of the full coding sequences for the mRNA corresponding to the selected ESTs, such as full-length cDNAs for the mammalian homocysteine-regulated sequences, such as dhc-1 shown in FIG. 5, makes possible the construction of isolated polynucleotides that can direct the expression of homocysteine-regulated gene products (proteins), fragments thereof, or analogs thereof. Further, the EST sequences of predetermined homocysteine-regulated mRNA species make possible the construction of nucleic acid hybridization probes and PCR primers that can be used to detect RNA and DNA sequences encoding the homocysteine-regulated gene products.

Polynucleotides encoding full-length protein or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual,* 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a homocysteine-regulated polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

Preferably, these amino acid sequences occur in the given order (in the amino-terminal to carboxy-terminal orientation) and may comprise other intervening and/or terminal sequences; generally such polypeptides are less than 1000 amino acids in length, more usually less than about 500 amino acids in lengths, and frequently approximately 200 amino acids in length. The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0). Isolated polynucleotides typically are less than approximately 10,000 nucleotide in length.

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting homocysteine-regulated RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to a predetermined homocysteine-regulated mRNA sequence is retained.

General PCR Methods

PCR synthesis can be performed using any suitable method. Generally it occurs in a buffered aqueous solution, preferably at a pH of 7–9, most preferably about 8. The bivalent primer(s) is/are added in suitable amounts (molar ratio to target), typically less than conventional PCR methods because of the self-priming nature of the overlapped concatemers. The deoxyribonucleoside triphosphates dATP, dCTP, dGTP and TTP are also added to the synthesis mixture in adequate amounts and the resulting solution is heated to about 85°–100° C. for from about 1 to 10 minutes, preferably from 1 to 4 minutes. After this heating period the solution is allowed to cool to from 20°–40° C., which is preferable for the primer hybridization. To the cooled mixture is added an agent for polymerization, and the reaction is allowed to occur under conditions known in the art. This synthesis reaction may occur at from room temperature up to a temperature above which the agent for polymerization no longer functions efficiently. Thus, for example, if DNA polymerase is used as the agent for polymerization, the temperature is generally no greater than about 45° C. The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of the primer and proceed in the 5' direction along the template strand, until synthesis terminates, producing molecules of different lengths.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

The steps of strand separation and extension product synthesis can be repeated as often as needed to produce the desired quantity of the specific nucleic acid sequence. The amount of the specific nucleic acid sequence produced will accumulate in an exponential fashion and the average size of the product will also increase as the length of the concatemers increases with each cycle.

Isolation of the Cognate Genes

Genomic gene clones or full-length cDNA clones corresponding to a homocysteine-regulated mRNA EST sequence are identified and isolated by screening a mammalian genomic or cDNA clone library, such as a human, rat, rabbit, or other genomic or cDNA library in yeast artificial chromosomes, cosmids, or bacteriophage λ (e.g., λ Charon 35), with a polynucleotide probe comprising a sequence of about at least 25 contiguous nucleotide (or their complement) of the EST cDNA sequence, such as that shown in FIG. 5 for dhc-1. Typically, hybridization and washing conditions are performed at high stringency according to conventional hybridization procedures. Positive clones are isolated and sequenced. For illustration and not for limitation, a full-length polynucleotide corresponding to the sequence of FIG. 5 may be labeled and used as a hybridization probe to isolate genomic clones from a human or murine genomic clone library in λEMBL4 or λGEM11 (Promega Corporation, Madison, Wis.); typical hybridization conditions for screening plaque lifts (Benton and Davis (1978) *Science* 196: 180) can be: 50% formamide, 5×SSC or SSPE, 1–5×Denhardt's solution, 0.1–1% SDS, 100–200 μg sheared heterologous DNA or tRNA, 0–10% dextran sulfate, $1\times10^5$ to $1\times10^7$ cpm/ml of denatured probe with a specific activity of about $1\times10^8$ cpm/μg, and incubation at 42° C.–37° C. for about 6–36 hours. Prehybridization conditions are essentially identical except that probe is not included and incubation time is typically reduced. Washing conditions are typically 1–3×SSC, 0.1–1% SDS, 50–70° C. with change of wash solution at about 5–30 minutes. For isolating mouse homocysteine-regulated protein polynucleotides with a human polynucleotide probe, it is often preferred to hybridize at approximately 39° C. and to wash sequentially at the following step temperatures: room temperature, 37° C., 39° C., 42° C., 45° C., 50° C., 55° C., 60° C., 65° C., and 70° C., stopping after each step and monitoring the background probe signal (and optionally detecting signal by autoradiogram and/or phosphor imaging, if radiolabeled probe is used) and terminating the washing steps when suitable signal/noise ratio is achieved, as determined empirically.

Other cDNAs and genomic clones (i.e., cognate nonhuman genes) can be analogously isolated from various non-human cDNA and genomic clone libraries available in the art (e.g., Clontech, Palo Alto, Calif.) by using probes based on the sequences shown in FIG. 5 with hybridization and washing conditions typically being less stringent.

Polynucleotides comprising sequences of approximately at least 30–50 nucleotides, preferably at least 100 nucleotide, corresponding to or complementary to the nucleotide sequences shown in FIG. 5 can serve as PCR primers and/or hybridization probes for identifying and isolating germline genes corresponding to the EST sequence. These germline genes may be human or may be from a related mammalian species, preferably rodents or primates. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIG. 5. Human genomic libraries are publicly available or may be constructed de novo from human DNA.

It is apparent to one of skill in the art that nucleotide substitutions, deletions, and additions may be incorporated into the polynucleotides of the invention. Nucleotide sequence variation may result from sequence polymorphisms of various alleles, minor sequencing errors, and the like. However, such nucleotide substitutions, deletions, and additions should not substantially disrupt the ability of the polynucleotide to hybridize to one of the polynucleotide sequences shown in FIG. 5 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 5) wherein the probe preferentially hybridizes to the specific target such that, for example, a single band corresponding to one or more of the RNA species (or alternatively spliced mRNA species) can be identified on a Northern blot of RNA prepared from a suitable cell source (e.g., a somatic cell). Polynucleotides of the invention and recombinantly produced homocysteine-regulated protein, and fragments or analogs thereof, may be prepared on the basis of the sequence data provided in FIG. 5 according to methods known in the art and described in Maniatis et al., *Molecular Cloning: A Laboratory Manual*, 2nd Ed., (1989), Cold Spring Harbor, N.Y. and Berger and Kimmel, *Methods in Enzymology, Volume 152, Guide to Molecular Cloning Techniques* (1987), Academic Press, Inc., San Diego, Calif., which are incorporated herein by reference.

Homocysteine-regulated polynucleotides may be short oligonucleotides (e.g., 20–100 bases long), such as for use as hybridization probes and PCR (or LCR) primers. These polynucleotide sequences may also comprise part of a larger polynucleotide (e.g., a cloning vector comprising a homocysteine-regulated protein clone) and may be fused, by polynucleotide linkage, in frame with another polynucleotide sequence encoding a different protein (e.g., glutathione S-transferase or β-galactosidase) for encoding expression of a fusion protein. Typically, homocysteine-regulated polynucleotides comprise at least 25 consecutive nucleotide which are substantially identical to a naturally-occurring homocysteine-regulated sequence (e.g., FIG. 5), more usually the polynucleotides comprise at least 50 to 100 consecutive nucleotide which are substantially identical to a naturally-occurring homocysteine-regulated sequence. However, it will be recognized by those of skill that the minimum length of a polynucleotide required for specific hybridization to a target sequence will depend on several factors: G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothiolate, etc.), among others.

If desired, PCR amplimers for amplifying substantially full-length cDNA copies may be selected at the discretion of the practitioner. Similarly, amplimers to amplify single exons or portions of the gene (murine or human) may be selected.

Each of these sequences may be used as hybridization probes or PCR amplimers to detect the presence of homocysteine-regulated mRNA, for example to diagnose a vascular disease characterized by the presence of an elevated or reduced homocysteine-regulated mRNA level in cells, or to perform tissue typing (i.e., identify tissues characterized by the expression of homocysteine-regulated mRNA), and the like. The sequences may also be used for detecting genomic homocysteine-regulated gene sequences in a DNA sample, such as for forensic DNA analysis (e.g., by RFLP analysis, PCR product length(s) distribution, etc.) or for diagnosis of diseases characterized by amplification and/or rearrangements of the gene. Alternatively, homocysteine-regulated polynucleotides, including ESTs, can be used as a foodstuff, combustible energy source, viscosity-enhancing solute, and the like. In a variation of the invention, polynucleotides of the invention are employed for diagnosis of pathological conditions or genetic disease that involve atherosclerosis, metabolic disorders, or other medical conditions related to homocysteine levels, and more specifically conditions and diseases that involve alterations in the structure or abundance of a homocysteine-regulated mRNA or gene product.

Antisense Polynucleotides

Additional embodiments directed to modulation of homocysteine metabolism or atherosclerosis include methods that employ specific antisense polynucleotides complementary to all or part of a predetermined homocysteine-regulated sequence, such as the sequences shown in FIG. 5), or a full-length genomic sequence. Such complementary antisense polynucleotides may include nucleotide substitutions, additions, deletions, or transpositions, so long as specific hybridization to the relevant target sequence corresponding to the subject mRNA or gene (e.g., FIG. 5) is retained as a functional property of the polynucleotide. Complementary antisense polynucleotides include soluble antisense RNA or DNA oligonucleotides which can hybridize specifically to mRNA species and prevent transcription of the mRNA species and/or translation of the encoded polypeptide (Ching et al. (1989) Proc. Natl. Acad. Sci. U.S.A. 86: 10006; Broder et al. (1990) Ann. Int. Med. 113: 604; Loreau et al. (1990) FEBS Letters 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of homocysteine-regulated polypeptides. Antisense polynucleotides that prevent transcription and/or translation of mRNA corresponding to homocysteine-regulated mRNA species may treat hyperhomocysteinemia, atherosclerosis, vascular disease, metabolic disorders, senescence, kidney and liver disorders, and the like, and/or reverse a metabolic phenotype of cells. Antisense polynucleotides of various lengths may be produced, although such antisense polynucleotides typically comprise a sequence of about at least 25 consecutive nucleotides which are substantially identical to a naturally-occurring homocysteine-regulated polynucleotide sequence, and typically which are identical to a sequence shown in FIG. 5 or a homocysteine-regulated sequence disclosed herein.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.).

Transgenic Animal Embodiments

Genomic clones of a homocysteine-regulated gene, particularly of the human or mouse dhc-1 gene, may be used to construct homologous targeting constructs for generating cells and transgenic nonhuman animals having at least one functionally disrupted allele. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated allele. Such mice may be sold commercially as research animals for investigation of homocysteine homeostasis, amino acid metabolism, atherosclerosis, immune system development, neoplasia, aging, and the like; the nonhuman animals may be used as pets, may be used for animal protein (foodstuff), and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a homocysteine-regulated cDNA or genomic gene copy may be used to construct transgenes for expressing polypeptides at high levels and/or under the transcriptional control of transcription control sequences which do not naturally occur adjacent to the homocysteine-regulated gene. For example but not limitation, a constitutive promoter (e.g., a HSV-tk or pgk promoter) or cell-lineage specific transcriptional regulatory sequence (e.g., an endothelial cell VEGF receptor promoter/enhancer) may be operably linked to a homocysteine-regulated polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods. Transgenic cells and/or transgenic nonhuman animals may be used to screen for anti-atherosclerotic agents and/or to screen for potential pro-atherosclerotic compounds.

Production of Homocysteine-Regulated Polypeptides

The nucleotide and amino acid sequences obtained from the disclosed methods enable those of skill in the art to produce polypeptides corresponding to all or part of the full-length polypeptide sequences encoded by mRNA species which are regulated by homocysteine. Such polypeptides may be produced in prokaryotic or eukaryotic host cells by expression of polynucleotides encoding the protein, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Fragments or analogs of a homocysteine-regulated protien may be prepared by those of skill in the art. Preferred amino- and carboxy-termini of fragments or analogs of occur near boundaries of functional domains.

One method by which structural and functional domains may be identified is by comparison of the nucleotide and/or amino acid sequence data to public or proprietary sequence databases. Preferably, computerized comparison methods are used to identify sequence motifs or predicted protein conformation domains that occur in other proteins of known structure and/or function. For example, the NAD-binding domains of dehydrogenases, particularly lactate dehydrogenase and malate dehydrogenase, are similar in conformation and have amino acid sequences that are detectably homologous (*Proteins, Structures and Molecular Principles*, (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the homocysteine-regulated sequences of the invention.

Additionally, computerized comparison of sequences identified by the disclosed method, such as shown in FIG. 5, to existing sequence databases can identify sequence motifs and structural conformations found in other proteins or coding sequences that indicate similar domains of the homocysteine-regulated protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a related sequences. Such homologous regions are candidate structural or functional domains. Examples include motifs present in other metabolic enzymes involved in amino acid metabolism. Alternatively, other algorithms are provided for identifying such domains from sequence data. Further, neural network methods, whether implemented in hardware or software, may be used to: (1) identify related protein sequences and nucleotide sequences, and (2) define structural or functional domains in homocysteine-regulated polypeptides (Brunak et al. (1991) *J. Mol. Biol.* 220: 49, which is incorporated herein by reference).

Although one class of preferred embodiments are fragments having amino- and/or carboxy-termini corresponding to amino acid positions near functional domains borders, alternative fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native homocysteine-regulated protein. However, analogs must comprise a segment of 25 amino acids that has substantial similarity to a portion of the amino acid sequences of a mammalian homocysteine-regulated protein. Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs. Analogs include various muteins of a sequence other than the naturally-occurring peptide sequence. For example, single or multiple amino acid substitutions (preferably conservative amino acid substitutions) may be made in the naturally-occurring sequence.

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W.H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

Fusion proteins of homocysteine-regulated proteins can be made, such as fusions with a GAL4 activation domain or DNA-binding domain, and the like, such as for two-hybrid screening systems.

Native homocysteine-regulated proteins, fragments thereof, or analogs thereof can be used as reagents in binding assays for identifying agents that interfere with homocysteine metabolism.

Production and Applications of Antibodies

Native homocysteine-regulated proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, N.Y., which is incorporated herein by reference.

For example but not for limitation, a recombinantly produced fragment of a homocysteine-regulated protein can be injected into a mouse along with an adjuvant following immunization protocols known to those of skill in the art so as to generate an immune response. Typically, approximately at least 1–50 μg of a homocysteine-related protein fragment or analog is used for the initial immunization, depending upon the length of the polypeptide. Alternatively or in combination with a recombinantly produced polypeptide, a chemically synthesized peptide having a homocysteine-regulated sequence may be used as an immunogen to raise antibodies which bind a homocysteine-regulated protein. Immunoglobulins which bind the recombinant fragment with a binding affinity of at least $1 \times 10^7$ $M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly-produced polypeptide (or chemically synthesized polypeptide) with an affinity of at least $1 \times 10^6$ $M^{-1}$. Animals other than mice and rats may be used to raise antibodies; for example, goats, rabbits, sheep, and chickens may also be employed to raise antibodies reactive with a homocysteine-regulated protein. Transgenic mice having the capacity to produce substantially human antibodies also may be immunized and used for a source of homocysteine-regulated protein antiserum and/or for making monoclonal-secreting hybridomas.

Bacteriophage antibody display libraries may also be screened for binding to a homocysteine-regulated polypeptide, such as a full-length protein, a fragment, or a fusion protein comprising a homocysteine-regulated polypeptide sequence.

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a homocysteine-regulated polypeptide that is immobilized (e.g., by covalent linkage to a chromatography resin to enrich for reactive phage by affinity chromatography) and/or labeled (e.g., to screen plaque or colony lifts).

Homocysteine-regulated polypeptides which are useful as immunogens, for diagnostic detection of antibodies in a sample, for diagnostic detection and quantitation of a homocysteine-regulated protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants.

For some applications of these antibodies, such as identifying immunocrossreactive proteins, the desired antiserum or monoclonal antibody(ies) is/are not monospecific. In these instances, it may be preferable to use a synthetic or recombinant fragment of a protein as an antigen rather than using the entire native protein. More specifically, where the object is to identify immunocrossreactive polypeptides that comprise a particular structural moiety, such as a DNA-binding domain, it is preferable to use as an antigen a fragment corresponding to part or all of a commensurate structural domain in the protein.

Yeast Two-Hybrid Screening Assays

An approach to identifying polypeptide sequences which bind to a predetermined polypeptide sequence has been to use a so-called "two-hybrid" system wherein the predetermined polypeptide sequence is present in a fusion protein (Chien et al. (1991) *Proc. Natl. Acad. Sci. (USA)* 88: 9578). This approach identifies protein-protein interactions in vivo through reconstitution of a transcriptional activator (Fields S and Song O (1989) *Nature* 340: 245), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site. Typically, the two-hybrid method is used to identify novel polypeptide sequences which interact with a known protein (Silver S C and Hunt S W (1993) *Mol. Biol. Rep.* 17: 155; Durfee et al. (1993) *Genes Devel.* 7; 555; Yang et al. (1992) *Science* 257: 680; Luban et al. (1993) *Cell* 73: 1067; Hardy et al. (1992) *Genes Devel.* 6; 801; Bartel et al. (1993) *Biotechniques* 14: 920; and Vojtek et al. (1993) *Cell* 74: 205). However, variations of the two-hybrid method have been used to identify mutations of a known protein that affect its binding to a second known protein (Li B and Fields S (1993) *FASEB J.* 7: 957; Lalo et al. (1993) *Proc. Natl. Acad. Sci.* (*USA*) 90: 5524; Jackson et al. (1993) *Mol. Cell. Biol.* 13; 2899; and Madura et al. (1993) *J. Biol. Chem.* 268: 12046). Two-hybrid systems have also been used to identify interacting structural domains of two known proteins (Bardwell et al. (1993) *Med. Microbiol.* 8: 1177; Chakraborty et al. (1992) *J. Biol. Chem.* 267: 17498; Staudinger et al. (1993) *J. Biol. Chem.* 268: 4608; and Milne G T and Weaver D T (1993) *Genes Devel.* 7; 1755) or domains responsible for oligomerization of a single protein (Iwabuchi et al. (1993) *Oncogene* 8; 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci.* (*USA*) 89: 4159). Alternatively, an *E. coli*/BCCP interactive screening system (Germino et al. (1993) *Proc. Natl. Acad. Sci.* (*U.S.A.*) 90: 933; Guarente L (1993) *Proc. Natl. Acad. Sci.* (*U.S.A.*) 90: 1639) can be used to identify interacting protein sequences (i.e., protein sequences which heterodimerize or form higher order heteromultimers).

Each of these two-hybrid methods rely upon a positive association between two Gal4 fusion proteins thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a calorimetric enzyme assay or (2) as enhanced cell growth on a defined medium (e.g., HIS3). A positive readout condition is generally identified as one or more of the following detectable conditions: (1) an increased transcription rate of a predetermined reporter gene, (2) an increased concentration or abundance of a polypeptide product encoded by a predetermined reporter gene, typically such as an enzyme which can be readily assayed in vivo, and/or (3) a selectable or otherwise identifiable phenotypic change in an organism (e.g., yeast) harboring the reverse two-hybrid system. Generally, a selectable or otherwise identifiable phenotypic change that characterizes a positive readout condition confers upon the organism either: a selective growth advantage on a defined medium, a mating phenotype, a characteristic morphology or developmental stage, drug resistance, or a detectable enzymatic activity (e.g., β-galactosidase, luciferase, alkaline phosphatase, and the like).

Transcriptional activators are proteins that positively regulate the expression of specific genes. They can be functionally dissected into two structural domains: one region that binds to specific DNA sequences and thereby confers specificity, and another region termed the activation domain that binds to protein components of the basal gene expression machinery (Ma and Ptashne (1988) *Cell* 55: 443). These two domains need to be physically connected in order to function as a transcriptional activator. Two-hybrid systems exploit this finding by hooking up an isolated DNA binding domain to one protein (protein X), while hooking up the isolated activation domain to another protein (protein Y). When X and Y interact to a significant extent, the DNA binding and activation domains will now be connected and the transcriptional activator function reconstituted (Fields and Song (1989) *Nature* 340: 245). The yeast host strain is engineered so that the reconstituted transcriptional activator drives the expression of a specific reporter gene such as HIS3 or lacZ, which provides the read-out for the protein-protein interaction (Field and Song (1989) op.cit.; Chein et al. (1991) op.cit.). One advantage of two-hybrid systems for monitoring protein-protein interactions is their sensitivity in detection of physically weak, but physiologically important, protein-protein interactions. As such it offers a significant advantage over other methods for detecting protein-protein interactions (e.g., ELISA assay).

The invention also provides host organisms (typically unicellular organisms) which harbor a homocysteine-regulated protein two-hybrid system, typically in the form of polynucleotides encoding a first hybrid protein, a second hybrid protein, and a reporter gene, wherein said polynucleotide(s) are either stably replicated or introduced for transient expression. In an embodiment, the host organism is a yeast cell (e.g., *Saccharomyces cervisiae*) and in which the reporter gene transcriptional regulatory sequence comprises a Gal4-responsive promoter.

Yeast comprising (1) an expression cassette encoding a GAL4 DNA binding domain (or GAL4 activator domain) fused to a binding fragment of a homocysteine-regulated protein (2) an expression cassette encoding a GAL4 DNA activator domain (or GAL4 binding domain, respectively) fused to a member of a cDNA library, and (3) a reporter gene (e.g., β-galactosidase) comprising a cis-linked GAL4 transcriptional response element can be used for screening for cDNA sequences encoding polypeptides which bind to the homocysteine-regulated protein with high affinity.

Yeast two-hybrid systems may be used to screen a mammalian (typically human) cDNA expression library, wherein cDNA is fused to a GAL4 DNA binding domain or activator domain, and a homocysteine-regulated polypeptide sequence is fused to a GAL4 activator domain or DNA binding domain, respectively. Such a yeast two-hybrid system can screen for cDNAs that encode proteins which bind to homocysteine-regulated sequences. For example, a cDNA library can be produced from mRNA from a human mature B cell (Namalwa) line (Ambrus et al. (1993) *Proc. Natl. Acad. Sci.* (*U.S.A.*)) or other suitable cell type. Such a cDNA library cloned in a yeast two-hybrid expression system (Chien et al. (1991) *Proc. Natl. Acad. Sci.* (*U.S.A.*) 88: 9578) can be used to identify cDNAs which encode proteins that interact with a homocysteine-regulated protein and thereby produce expression of the GAL4-dependent reporter gene. Polypeptides which interact with a homocysteine-regulated protein can also be identified by immunoprecipitation of the homocysteine-regulated protein with antibody and identification of co-precipitating species. Further, polypeptides that bind a homocysteine-regulated protein can be identified by screening a peptide library (e.g., a bacteriophage peptide display library, a spatially defined VLSIPS peptide array, and the like) with a homocysteine-regulated polypeptide.

Once such cDNAs encoding such interacting polypeptides are identified, they may be used for screening a bank of compounds (e.g., small molecule libraries) to identify agents which inhibit the binding interaction. Yeast comprising (1) an expression cassette encoding a GAL4 DNA binding domain (or GAL4 activator domain) fused to a binding fragment of homocysteine-regulated protein (2) an expression cassette encoding a GAL4 DNA activator domain (or GAL4 binding domain, respectively) fused to the selected cDNA encoding the interacting protein, and (3) a reporter gene (e.g., β-galactosidase) comprising a cis-linked GAL4 transcriptional response element can be used for screening for agents which inhibit the cDNA-encoded polypeptide from binding to the homocysteine-regulated protein with high affinity. Such yeast are incubated with a test agent and expression of the reporter gene (e.g., β-galactosidase) is determined; the capacity of the agent to inhibit expression of the reporter gene as compared to a control culture identifies the agent as a candidate atherosclerosis modulating agent.

Administration of an efficacious dose of an agent capable of specifically inhibiting gene expression related to hyperhomocysteinemia to a patient can be used as a therapeutic or prophylactic method for treating pathological conditions (e.g., hyperhomocysteinemia, atherosclerosis, and the like) which are effectively treated by modulating cellular responsiveness to homocysteine.

Methods for Forensic Identification

The homocysteine-regulated polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, and the like) and subjected to RFLP analysis, allele-specific PCR, or PCR cloning and sequencing of the amplification product to determine the structure of the homocysteine-regulated gene region. On the basis of the homocysteine-regulated gene structure, the individual from which the sample originated will be identified with respect to his/her homocysteine-regulated protein genotype. The homocysteine-regulated protein genotype may be used alone or in conjunction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g., see New England Biolabs 1995 catalog). Corresponding digestion products from each individual are loaded separately on an electrophoretic gel (typically agarose), electrophoresed, blotted to a membrane by Southern blotting, and hybridized with a labeled homocysteine-regulated probe (e.g., FIG. 5). Restriction fragments (bands) which are polymorphic among members of the population are used as a basis to discriminate homocysteine-regulated protein genotypes and thereby classify individuals on the basis of their homocysteine-regulated protein genotype.

Similar categorization of homocysteine-regulated genotypes may be performed by sequencing PCR amplification products from a population of individuals and using sequence polymorphisms to identify alleles (genotypes), and thereby identify or classify individuals.

The invention also provides homocysteine-regulated polynucleotide probes for diagnosis of disease states (e.g., hyperhomocysteinemia, atherosclerosis) by detection of a homocysteine-regulated mRNA in cells explanted from a patient, or detection of a pathognomonic homocysteine-regulated gene allele (e.g., by RFLP or allele-specific PCR analysis) which predisposes to hyperhomocysteinemia or atherosclerosis. Typically, the detection will be by in situ hybridization using a labeled (e.g., $^{32}P$, $^{35}S$, $^{14}C$, $^{3}H$, fluorescent, biotinylated, digoxigeninylated) homocysteine-regulated polynucleotide, although Northern blotting, dot blotting, or solution hybridization on bulk RNA or poly $A^+$ RNA isolated from a cell sample may be used, as may PCR amplification using homocysteine-regulated protein specific primers. Cells which contain an altered amount of a homocysteine-regulated mRNA as compared to normal cells of the same cell type(s) will be identified as originating from disease candidates. Similarly, the detection of pathognomonic rearrangements or amplification of the homocysteine-regulated gene locus or closely linked loci in a cell sample will identify the presence of a pathological condition or a predisposition to developing a genetically linked pathological condition (e.g., cancer, genetic disease). The polynucleotide probes are also used for forensic identification of individuals, such as for paternity testing or identification of criminal suspects or unknown decedents.

Homocysteine-Reponsive Transcription Elements

A transcriptional regulatory sequence can be isolated from an endogenous homocysteine-regulated gene, typically by genomic DNA cloning. In such genes, the transcriptional regulatory sequence is at least the minimal sequence(s) required for efficient homocysteine-induced or homocysteine-repressed expression, which generally is at least a promoter and at least about 0.2 kilobase (kb) upstream of the promoter, preferably at least about 1 to 3 kb upstream of the promoter, more preferably at least about 5 kb upstream of the promoter, and frequently at least about 8 or more kb upstream of the promoter. Frequently, sequences downstream of the promoter, especially intronic sequences, are included. Reporter constructs can be made. Usually the sequences upstream of the promoter are used contiguously, although various deletions and rearrangements can be employed. Some desired regulatory elements (e.g., enhancers, silencers) may be relatively position-insensitive, so that the regulatory element will function correctly even if positioned differently in a reporter construct than in the corresponding germline gene. For example, an enhancer may be located at a different distance from a promoter, in a different orientation, and/or in a different linear order. For example, an enhancer that is located 3' to a promoter in germline configuration might be located 5' to the promoter in a reporter construct. Where convenient, it is preferred that a contiguous segment of genomic DNA sequence spanning the homocysteine-regulated gene and containing as much upstream flanking sequence as convenient (typically at least about 1–10 kb) be used in the reporter construct or a gene therapy construct. It is further recognized that a homocysteine-regulated gene may comprise multiple promoters, which may individually be cell-specific.

Diagnostic and Therapeutic Applications

A change (typically an increase) in the level of a homocysteine-regulated mRNA in cells of in a biological sample from an individual which is outside the range of clinically established normal levels indicates the presence of an active disease or condition (e.g., hyperhomocysteinemia, atherosclerosis, and the like) in the individual from whom the sample was obtained and/or indicates a predisposition of the individual for developing (or progressing through) the disease. Thus, detection of a pathognomonic concentration (relative abundance in an mRNA pool, such as may be standardized to GAPDH) of a homocysteine-regulated mRNA in a patient sample, such as a blood, biopsy, serum, saliva, or buccal cell sample, is an indicator of hyperhomocysteinemia and atheroscleotic disease.

Further, a homocysteine-regulated mRNA may be used as a differentiation marker to identify and type cells of certain lineages and developmental origins. Such cell-type specific detection may be used for histopathological diagnosis of neoplasms (e.g., for diagnosing the cell type and/or differentiation state of a primary tumor cell) or other applications (e.g., localizing imaging or toxic agents to specific locations for magnetic imaging or radioimaging in vivo or for cytotoxic effect). Such agents may include, for example, a linked component comprising: metals, chemotherapeutic drugs, radiosensitizing agents, cellular toxins, radionuclides, and others.

Various other applications of such agents that specifically detect a homocysteine-regulated mRNA or the encoded protien are apparent to those of skill in the art and may be developed.

Detection of Homocysteine-Regulated Genes
Samples

The identification and measurement of a homocysteine-regulated mRNA or the encoded protein in a biological sample can be performed by one or more assay methods of the invention. The general scheme of such an assay method requires that a biological sample is obtained from a human patient. The biological sample is typically a cellular sample, such as blood, tissue biopsy material, or buccal scapings, may be used.

Antibody Embodiment

Although many variations of the invention are possible, including assays using a single antibody that is essentially monospecific for a homocysteine-regulated protien and competitive immunoassays, a two-component sandwich binding assay is believed to be generally preferable. In one embodiment of a sandwich binding assay, an immobilized binding component binds to a site on a homocysteine-regulated protein and a soluble labeled binding component binds to a second site on the homocysteine-regulated protien, unbound components are removed (typically by washing with a suitable buffered solution and/or centrifugation), and the amount of labeled binding component that remains immobilized via linkage through the analyte (i.e., the homocysteine-regulated protein) is quantitatively measured to determine the amount of homocysteine-regulated protein present in the sample. Some sandwich assays require addition of immobilized binding component and analyte (i.e., sample) followed by separation of bound and unbound analyte, then followed by addition of soluble labeled binding component.

Using the methods disclosed herein, others skilled in the art can readily produce suitable immunological reagents. Moreover, methods (Kohler and Milstein (1976) *Eur. J. Immunol.* 6: 511, incorporated herein by reference) are known for producing a monoclonal antibody, such as one that binds to a a homocysteine-regulated protein with an affinity of typically at least about $1\times10^6$ $M^{-1}$, preferably at least about $1\times10^8$ $M^{-1}$, and more preferably at least about $1\times10^9$ to $1\times10^{11}$ $M^{-1}$ or ore, and which has a binding affinity for a non-specific proteins of at least about 10-fold less, preferably at least about 100- to 1000-fold less, with a sufficient difference in binding affinity between the homocysteine-regulated protein and the remaining protein pool so as to be a specific binding component. In general terms, such a method comprises the steps of: (1) immunizing an animal with a composition containing an immunogenic dose of a homocysteine-regulated protein (or a fragment thereof), usually at least about 50 to 500 ug of purified material, typically co-administered with an adjuvant, (2) harvesting B-cells from the animal, (3) fusing the B-cells with a myeloma to generate a bank of hybridoma clones, and (4) selecting, from the bank, a hybridoma clone that expresses a monoclonal antibody which binds to the homocysteine-regulated protein with an affinity of at least about $1\times10^7$ $M^{-1}$ and which has a binding affinity for nonfat milk and calf serum of at least about 10- to 1000-fold lower.

Additionally, a method for producing a polyclonal antiserum that specifically or preferentially binds to a homocysteine-regulated protein is described. In general, such a polyclonal antiserum will have an affinity for the homocysteine-regulated protein of at least $1\times10^8$ $M^{-1}$ and which has a binding affinity for nonfat milk solids of at least about 10- to 1000-fold lower, comprising the steps of: (1) immunizing an animal with a composition containing an immunogenic dose of a homocysteine-regulated protein or a fragment thereof (and typically an adjuvant), (2) obtaining a polyclonal antiserum from said animal, (3) preadsorbing said polyclonal antiserum with a saturating amount of a nonfat milk solids or serum, and (4) recovering antibodies that do not substantially bind to the nonfat milk solids or serum.

Detection of bound "sandwich" complexes typically is performed by detecting the presence of bound labeled binding component. Usually, the labeled binding component comprises a direct label, such as a fluorescent label, radioactive label, or enzyme-conjugated label that catalyzes the conversion of a chromogenic substrate to a chromophore. However, it is possible, and often desirable for signal amplification, for the labeled binding component to be detected by at least one additional binding component that incorporates a label. Signal amplification can be accomplished by layering of reactants where the reactants are polyvalent. Direct labeling of binding components may be accomplished by various methods known in the art, including: covalent attachment of various enzymes (e.g., horseradish peroxidase, $\beta$-galactosidase, and alkaline phosphatase), fluorescent molecules (fluorescein isothiocyanate, rhodamine, dansyl chloride), and radioactive materials ($^3H$, $^{14}C$, $^{32}P$, $^{35}S$, $^{125}I$, $^{131}I$) which may be incorporated as labeled amino acid residues or post-translationally labeled (e.g., Chloramine T method).

Diagnostic Kits

The invention also encompasses diagnostic kits that typically contain the assay reagents in a prepackaged form. The assay components will typically include homocysteine-regulated protein binding component, typically a specifically reactive antibody, and a labeled component (which may be attached or incorporated into the homocysteine-regulated protein binding component or may be provided separately), a suitable reaction vessel (e.g., a microtiter well, a polymer membrane), and may also include diluent(s), assay buffer(s), wash buffer(s), and development reagents (e.g., chromogenic substrate for enzyme-linked assays). The various assay components are usually provided in aqueous solution, but may be provided in lyophilized form and reconstituted for performing the assay. Similarly, automated devices may be developed to perform assays of the invention.

The following examples are given to illustrate the invention, but are not to be limiting thereof. All percentages given throughout the specification are based upon weight unless otherwise indicated. All protein molecular weights are based on mean average molecular weights unless otherwise indicated.

EXPERIMENTAL EXAMPLES

Overview

Figures 2A, 2B:
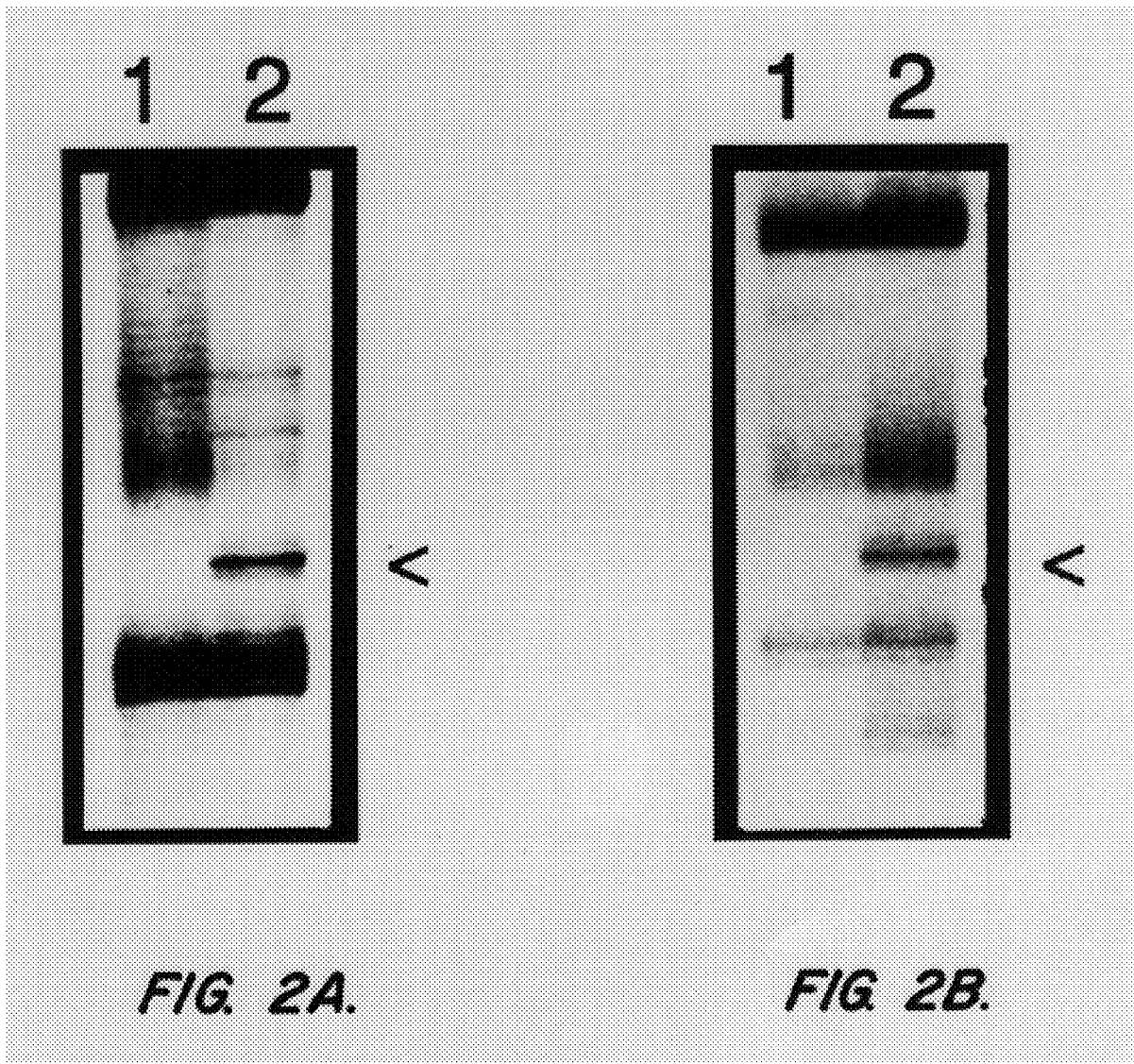
FIGS. 2A–2B. Identification of a homocysteine-inducible gene showing reproducibility by mRNA differential display. Total RNA from Dami cells, treated for 18 hr with 0 (lane 1) or 1.0 mM (lane 2) homocysteine, was DNase-treated and subjected to mRNA differential display using primers (SEQ ID NO:9) 5'-T$_{(11)}$MG-3' (SEQ ID NO:4) and 5'-AGCCAGCGAA-3'. The radiolabelled cDNA fragments were then resolved on 6% sequencing gels. The arrowhead marks the homocysteine-inducible gene (designated dhc-1) which is reproducibly amplified in two separate experiments (compare panels A and B).
Figure 3A:
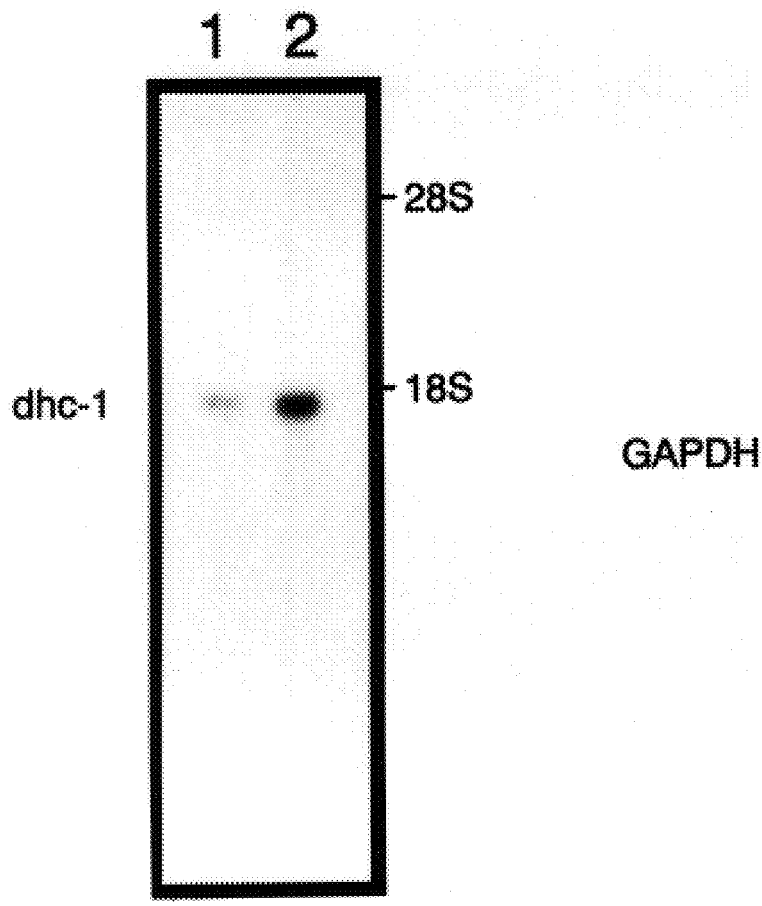
FIGS. 3A–3B. Northern blot analysis using the cDNA fragment dhc-1 as a probe. Total RNA from Dami cells treated for 18 hr with 0 (lane 1) or 1.0 mM (lane 2) homocysteine was separated on a formaldehyde/1.2% agarose gel. cDNA fragment dhc-1 was labeled by random priming and hybridized as described infra. dhc-1 hybridizes specifically to a 1.8 kb transcript showing homocysteine-dependent upregulation (panel A). As an RNA loading control the same blot was reprobed with a GAPDH cDNA (panel B).
Figure 3B:
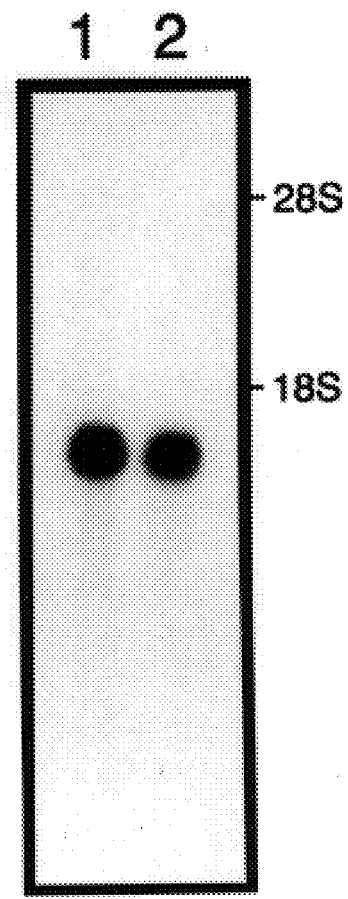
Figure 4:
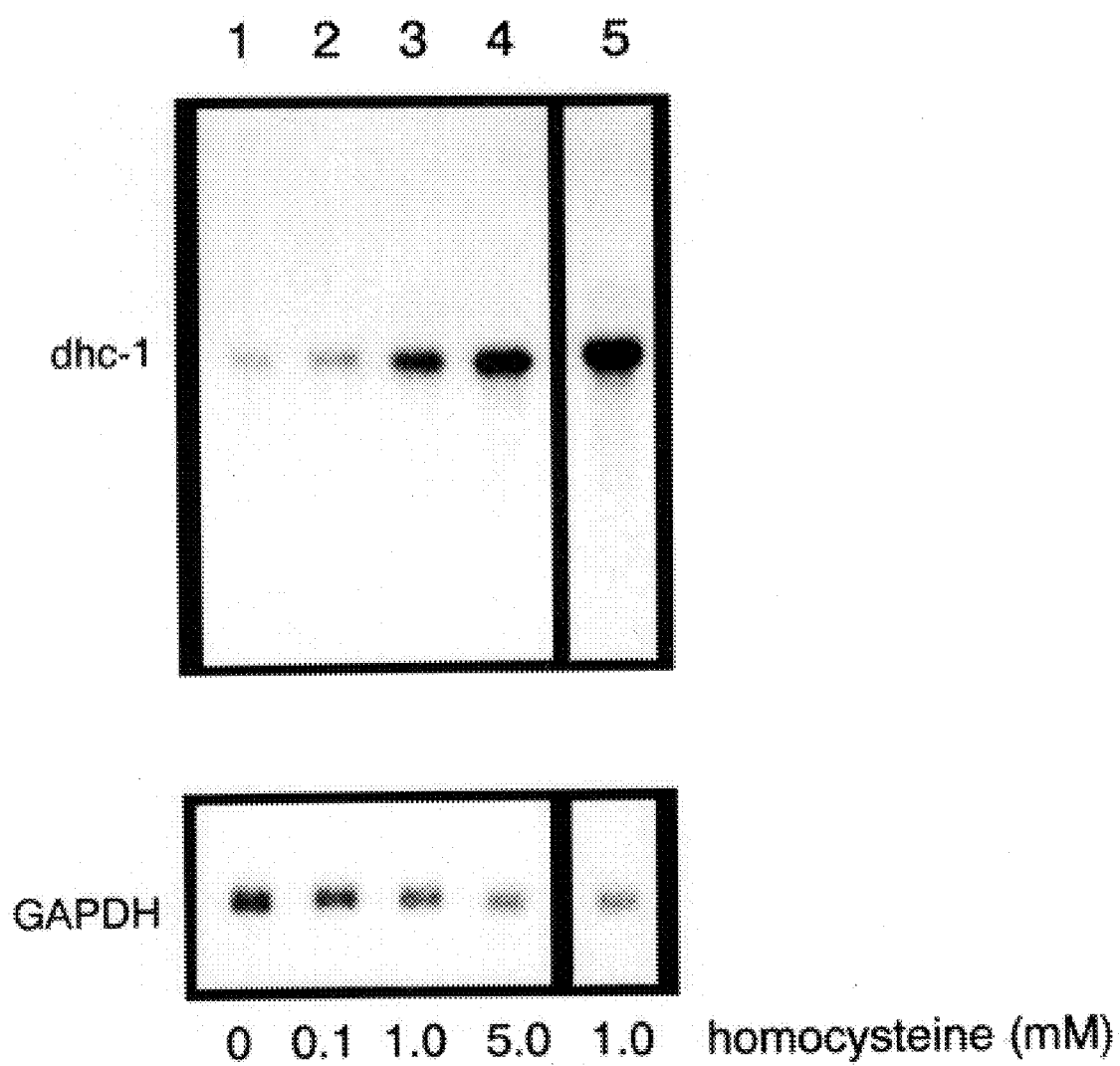
FIG. 4(A). Northern blot analysis on HUVECs treated with homocysteine and probed with dhc-1. Total RNA from HUVECS, treated for 18 hr with 0, 0.1, 1.0 and 5.0 mM homocysteine (lanes 1 to 4, respectively) or 2 hr with 1.0 mM homocysteine (lane 5), was separated on a formaldeyde/1.2% agarose gel. cDNA fragment dhc-1 was labeled by random priming and hybridized as described infra. dhc-1 hybridizes specifically to a 1.8 kb transcript showing dose-dependent upregulation in response to homocysteine. The 1.8 kb transcript was also induced in HUVECs treated for 2 hr with 1 mM homocysteine (lane 5).
FIG. 4B. As a RNA loading control, the same blot was reprobed with a GAPDH cDNA.

At present, there is no simple, reliable and/or quick test to identify individuals with hyperhomocysteinemia. In addition, plasma homocysteine levels in individuals heterozygous for cystathionine β-synthase (the major inherited form of hyperhomocysteinemia) can overlap with those of healthy individuals, thus complicating the identification of those at risk for premature atherosclerosis. In addition, strategies to monitor and improve this condition are lacking due to the poor understanding of the mechanisms responsible for homocysteine-induced vascular disease. The examples identify homocysteine-induced genes and their gene products for the successful diagnosis and treatment of homocysteine-induced vascular disease.

mRNA differential display (Liang and Pardee, 1992, supra; Liang et al. 1993) was used to identify specific homocysteine-induced genes in human umbilical vein endothelial cells (HLJVECs) and the human megakaryocytic cell line Dami exposed to homocysteine. Briefly, mRNA differential display patterns from HLTVECs and Dami cells exposed to homocysteine were compared on 6% sequencing gels to identify differentially expressed cDNA fragments (FIG. 1). Homocysteine-induced cDNA fragments were defined as those fragments that were specifically and reproducibly up-regulated on differential display gels. Approximately 10–20 cDNA fragments have been identified in HUVECs and Dami cells as homocysteine-induced genes. One of these, designated dhc-1, was consistently induced in Dami cells treated with homocysteine (FIG. 2). To confirm the homocysteine-induced up-regulation pattern observed on the differential display gels, the selected cDNA fragments, including dhc-1, were recovered, reamplified and used to probe Northern blots prepared with total RNA isolated from HUVECs and Dami cells treated in the presence or absence of homocysteine. dhc-1 was shown to specifically hybridize to a 1.8 kb transcript on Northern blots that reproduced the homocysteine-specific increase in expression (FIG. 3). dhc-1 was also shown to be up-regulated, in a dose-dependent manner, in HUVECs exposed to increasing concentrations of homocysteine (FIG. 4). Cloned cDNA fragments that showed homocysteine-dependent up-regulation on Northern blots were subsequently cloned into pBluescript (Clontech, Palo Alto, Calif.) and partially sequenced using T3 or T7 sequencing primers. The partial nucleotide sequence of dhc-1 is shown in FIG. 5. Searching of the GenBank database revealed that dhc-1 has 96% homology to a novel human cDNA, HHCJ64 (accession #M62278). The function of this gene is not known, however, its origin may be mitochondrial. This same approach, from identifying homocysteine-induced cDNA fragments on differential gels to searching GenBank for homology to other genes, is being used to characterize the additional homocysteine-induced genes that have been identified in HUVECs and Darni cells.

Thus, the example indicates successful identification of specific homocysteine-induced genes expressed in endothelial cells and megakaryocytes. These sequences are be used to successfully identify individuals predisposed to elevated levels of blood homocysteine. Secondly, it provides a means of identifying whether or not treatments which are supposedly known to decrease homocysteine levels actually result in the reduction of endothelial cell injury which is responsible for the atherosclerotic effects of homocysteine. In addition, by identifying these homocysteine-induced genes and their gene products it is possible to better understand the mechanisms involved in homocysteine-induced vascular disease. Furthermore, these genes and their gene products allow detection and improve the outcome of premature vascular disease and thrombosis, regardless of its origin.

Example 1 mRNA differential display, followed by Northern blot analysis was used to identify homocysteine-induced genes expressed in HUVECs and Dami cells. HUVECs were used in these studies because previous data has shown that homocysteine is cytotoxic to the endothelium. In addition, endothelial damage followed by vascular occlusion are common and are the usual cause of premature death in patients homozygous for cystathionine β-synthase. Dami cells, a megakaryocytic cell line were used because of the ease at which platelets can be isolated and analyzed. Thus, specific homocysteine-induced genes expressed in megakaryocytes are detected by isolating platelets. The method of differential display involves the reverse transcription of mRNAs with oligo-dT primers containing additional nucleotides which anchor the primer to the beginning of the poly(A) tail, followed by a PCR reaction in the presence of an arbitrary 10-I 5 mer and the original anchor primer. The amplified cDNA subpopulations are then separated on denaturing sequencing gels to identify homocysteine-induced cDNAs. Once these cDNAs are shown to be reproducibly up-regulated on differential display gels, they are removed from the gel, PCR-amplified and used as probes on Northern blots to confirm their homocysteine-induced expression. These homocysteine-induced cDNA fragments are then sequenced and compared to the GenBank databases to determine if these cDNAs are novel or have been identified previously. The cDNA fragments of interest can also be used as probes to screen appropriate cDNA libraries for the complete gene of interest. Once cloned, the open reading frame of the cDNAs of interest can be expressed as recombinant fusion proteins in bacteria and used as immunogens for the production of specific polyclonal or monoclonal antibodies directed to the specific gene product. As a result, homocysteine-induced expression of these gene products can be easily determined. The Materials and Methods used to identify these homocysteine-induced genes from HUVECs and Dami cells are described in detail below, Cell Culture Dami cells were obtained from the American Type Culture Collection (ATCC) (Rockville, Md.) and cultured in 75 ml flasks in RPMI 1640 medium supplemented with 5% heat-inactivated fetal bovine serum, 100 U/ml penicillin and 100 $\mu$g/ml streptomycin. Endothelial cells were obtained from fresh human umbilical veins and routinely cultured in 75 ml$^2$ flasks coated with human fibronectin (5 $\mu$g/cm$^2$) in M199 medium containing 10% fetal calf serum, 100 IU penicillin, 100 $\mu$g/ml streptomycin, 100 $\mu$g/ml heparin and 30 $\mu$g/ml endothelial cell growth supplement. Cultures were maintained at 37° C. in a humidified atmosphere of 5% CO$_2$ in air. DL-homocysteine (Sigma, St. Louis, Mo.) was prepared in sterile water, filtered and added to 60% confluent cell cultures at the desired concentration (0.1 to 5 mM). After incubation for 18 hr with control or homocysteine-containing media, cells were washed twice with sterile PBS prior to RNA isolation.

Total RNA Isolation and Purification

All solutions were prepared with water that had been treated with 0.1% diethyl pyrocarbonate (DEPC) and autoclaved prior to total RNA isolation. Total RNA was isolated from cultured cells using the RNeasy total RNA kit as described by the manufacturer (Qiagen, Chatsworth, Calif.) and resuspended in DEPC-treated water. DNA contamination was removed by incubating the samples with 2 U of RQ DNase (Promega, Madison, Wis.) in the presence of 12 U of Rnasin (Promega) for 30 min at 37° C. After the addition of DEPC-treated water to 100 $\mu$l, the samples were mixed with an equal volume of phenol/chloroform (3:1), centrifuged and the aqueous phase transferred to an RNase-free 1.7 ml centrifuge tube. After the addition of 10 $\mu$l of 3 M sodium acetate and 300 μl of absolute ethanol, the RNA was precipitated overnight at −80° C. The RNA was collected by centrifugation at 14,000×g for 10 min at 40° C., washed briefly with 85% ethanol, dried and resuspended in DEPC-treated water. The A260/280 ratio was determined and used to calculate the amount and purity of each RNA sample. The RNA samples were subsequently resuspended in 10 μg aliquots and stored at −80° C.

mRNA Differential Display

After removal of DNA contamination from the total RNA samples, differential display was carried out using the RNA map and image kits (GenHunter, Brookline, Mass.) as described by the manufacturer. The cDNAs were amplified by PCR in the presence of α-$S^{35}$ dATP (specific activity>1000 Ci/mnol; NEN, Toronto, ON) using a Perkin-Elmer 480 thermal cycler. Parameters for the 40-cycle PCR were as follows: denaturation at 94° C. for 30 sec, annealing at 40° C. for 120 sec and extension at 72° C. for 30 sec. Following the PCR, DNA loading buffer (GenHunter) was added to 4 μl of each reaction mixture and heated to 80° C. for 2 min. The radiolabelled PCR amplified cDNA fragments were then resolved on a 6% sequencing gel run at 55 W constant temperature. The gels were dried without fixation onto Whatman 3M filter paper and exposed to Kodak XAR-5 film for approximately 1–3 days at room temperature. cDNA fragments which were shown to be clearly up-regulated in the presence of homocysteine were subsequently confirmed by repeat differential display reactions using total RNA isolated from new cell cultures treated as described previously.

Recovery and Reamplification cDNA Fragments cDNA fragments showing reproducible up-regulation were excised from the differential display gels using a sterile scalpel blade. Gel slices were then placed in 100 μl of water for 10 min and heated to 100° C. for 15 min. The tubes were spun in a microcentrifuge at 14,000×g for 2 min and the supernatant transferred to a new microfuge tube. The cDNA fragments were ethanol precipitated in the presence of glycogen, washed with 85% ethanol and resuspended in 10 μl of water. For reamplification, 4 μl of each sample was used. PCR conditions were as described above using the appropriate primer sets and conditions except that the dNTP concentration was 20 μM and no α-$S^{35}$ dATP was present. The amplified cDNA fragments were subsequently purified from 1% agarose gels using the Qiaex gel extraction kit (Qiagen, Chatsworth, Calif.) and used directly as probes on Northern blots.

Northern Blot Analysis

DNase-free total RNA (10 μg) from control and homocysteine-treated cells were fractionated on 2.2M formaldehyde/1.5% agarose gels and transferred overnight onto Zeta-Probe GT nylon membranes (Bio-Rad, Toronto, ON) in 50 mM NaOH. The RNA was crosslinked to the membrane using a Stratalinker UV crosslinker (PDI Bioscience, Toronto, ON) prior to hybridization. Specific probes were generated by labelling the reamplified or cloned cDNA fragments with [α-$P^{32}$]-dCTP (ICN, Mississauga, ON) using a random primer DNA labelling kit (Boehringer Mannheim, Laval, QC). After overnight hybridization at 42° C., the filters were washed twice in 2×SSC/0.1% SDS, followed by two washes at 55° C. for 15 min in 0.1×SSC/0.1% SDS. The membranes were then sealed in plastic wrap and exposed to Kodak X-Omat AP film at −80° C. for approximately 1–3 days. Hybridization of the same blot with a partial cDNA fragment of human glyceraldehyde 3-phosphate dehydrogenase (GAPDH) was used as a loading control. The quantification of changes in the expression of the homocysteine-dependent transcripts was performed using an UltroScan XL laser densitometer (Pharmacia, Bale d'Urfe, QC).

Cloning and Sequencing of cDNA Fragments cDNA fragments which showed differential expression on Northern blots were then subcloned into T-ended pBluescript (KS) and sequenced using a modified T7 polymerase system (Sequenase Version 2, USB, Cleveland, Ohio) with either T7 or T3 primers. The cDNA sequences were analyzed for homology with the EMBL and GenBank DNA databases using the DNASIS DNA sequencing analysis system (Hitachi, Brisbane, Calif.).

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

What is claimed is:

1. A method for diagnosing an individual having hyperhomocysteinemia and/or a predisposition to developing premature atherosclerosis, comprising:

identifying, from a pool of individuals, an individual having elevated levels of serum homocysteine by determining the relative expression level of at least one homocysteine-regulated mRNA or protein encoded therein in a cellular sample obtained from the individual, whereby a relative expression level of the homocysteine-regulated mRNA or protein is in a predetermined pathognomonic range and the individual is thereby identified as an atherosclerosis disease candidate and a hyperhomocystenemia candidate.

2. The method of claim 1, wherein the homocysteine-regulated mRNA or protein is a protein encoded by an mRNA comprising a predetermined sequence of at least 30 nucleotides and known to be regulated by homocysteine.

3. The method of claim 1, wherein the relative expression level of the homocysteine-regulated protein is performed by an immunoassay for quantitative analysis of a homocysteine-regulated protein, wherein the immunoassay comprises an antibody predetermined to specifically bind to the homocysteine-regulated protein.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (xi) SEQUENCE DESCRIPTION: SEQ ID NO:1:

AAGCTTGATT GCC                                                13

(2) INFORMATION FOR SEQ ID NO:2:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (xi) SEQUENCE DESCRIPTION: SEQ ID NO:2:

AAGCTTCGAC TGT                                                          13

(2) INFORMATION FOR SEQ ID NO:3:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (xi) SEQUENCE DESCRIPTION: SEQ ID NO:3:

AAGCTTTGGT CAG                                                          13

(2) INFORMATION FOR SEQ ID NO:4:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:4:

AGCCAGCGAA                                                              10

(2) INFORMATION FOR SEQ ID NO:5:

(i) SEQUENCE CHARACTERISTICS:
            (A) LENGTH: 119 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

AAATCAGAAT AGGTGTTGGT ATAGAATGGG GTCTCCTCCT CCGGCGGGGT CGAAGAAGGT        60

GGTGTTGAGG TTGCGGTGAG GTTTTGATCA CTCTGGGTGA CAGAGTGAGA CCCTGTCCC       119

(2) INFORMATION FOR SEQ ID NO:6:

(i) SEQUENCE CHARACTERISTICS:
            (A) LENGTH: 119 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

AAATCAGAAT AGGTGTTGGT ATAGAATGGG GTCTCCTCCT CCGGCGGGGT CGAAGAAGGT        60

GGTGTTGAGG TTGCGGTCTG TTAGTAGTAT AGTGATGCCA GCAGCTAGGA CTGGGAGAG       119

(2) INFORMATION FOR SEQ ID NO:7:

(i) SEQUENCE CHARACTERISTICS:
            (A) LENGTH: 56 base pairs
            (B) TYPE: nucleic acid
            (C) STRANDEDNESS: single
            (D) TOPOLOGY: linear

```
        (ii) MOLECULE TYPE: DNA (genomic)

(xi) SEQUENCE DESCRIPTION: SEQ ID NO:7:

AAGCTAAGCT AAGCTAAGCT AAGCTAAGCT AAGCTAAGCT AAGCTAAGCT AAGCTC               56

(2) INFORMATION FOR SEQ ID NO:8:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

AAGCTAAGCT AAGCTAAGCT AAGCTAAGCT AAGCTAAGCT AAGCTAAGCT AAGCTT               56

(2) INFORMATION FOR SEQ ID NO:9:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

TTTTTTTTTT TMG                                                              13
```